(12) United States Patent
Hebeisen et al.

(10) Patent No.: US 6,844,345 B2
(45) Date of Patent: Jan. 18, 2005

(54) PIPERAZINE DERIVATIVES

(75) Inventors: Paul Hebeisen, Basel (CH); Patrizio Mattei, Riehen (CH); Marc Muller, St. Louis (FR); Hans Richter, Grenzach-Wyhlen (DE); Stephan Roever, Inzlingen (DE); Sven Taylor, Riedisheim (FR)

(73) Assignees: Hoffman-La Roche Inc., Nutley, NJ (US); Vernal Research Limited, Winnersh, Vernalis (GB)

( * ) Notice: Subject to any disclaimer, the term of this patent is extended or adjusted under 35 U.S.C. 154(b) by 0 days.

(21) Appl. No.: 10/092,751

(22) Filed: Mar. 7, 2002

(65) Prior Publication Data

US 2002/0169163 A1 Nov. 14, 2002

(30) Foreign Application Priority Data

Mar. 13, 2001 (GB) .............................. 0106177

(51) Int. Cl.$^7$ .................. A61K 31/4985; C07D 487/04
(52) U.S. Cl. ........................ 514/250; 514/249; 544/343; 544/344
(58) Field of Search ................................ 544/343, 344; 514/249, 250

(56) References Cited

U.S. PATENT DOCUMENTS

| | | | |
|---|---|---|---|
| 3,317,524 A | 5/1967 | Freed | |
| 4,598,089 A | 7/1986 | Hadvary et al. | |
| 5,854,245 A | 12/1998 | Duggan et al. | |
| 6,004,996 A | 12/1999 | Shah et al. | |
| 2003/0216401 A1 * | 11/2003 | Bentley et al. | .............. 514/250 |

FOREIGN PATENT DOCUMENTS

| | | |
|---|---|---|
| EP | 185 359 | 6/1986 |
| EP | 189 577 | 8/1986 |
| EP | 443 449 | 8/1991 |
| EP | 524 495 | 1/1993 |
| EP | 0 572 863 | 12/1993 |
| WO | WO 96/12721 | 5/1996 |
| WO | WO 99/34786 | 7/1999 |
| WO | WO 00/09122 | 2/2000 |
| WO | WO 00/09123 | 2/2000 |
| WO | WO 00/44753 | 8/2000 |
| WO | WO 02/10169 | 2/2002 |

OTHER PUBLICATIONS

Parker, "Obesity: Trends and Treatments", Scrip Reports, PJB Publications Limited, (1996).
Kennett et al., Psychopharmacology, 96, pp. 93–100 (1988).
Kennett et al., Eur. J. Pharmacol., 141, pp. 429–435 (1987).
Kitchener et al., Psychopharmacology, 113, pp. 369–377 (1994).
Walsh et al., Psychopharmacology, 116, pp. 120–122 (1994).
Sargeant et al., Psychopharmacology, 133, pp. 309–312 (1997).
Tecott et al., Nature, vol. 374, pp. 542–546 (1995).
Kennett et al., Neuropharmacology, vol. 36, pp. 609–620 (1997).
Hoyer et al., European J. Pharmacology, 118, pp. 13–23 (1985).
Schmuck et al., FEBS Letters, 342, pp. 85–90 (1994).
McKenna et al., J. Neuroscience, 9, pp. 3482–3490 (1989).
Rajur et al., Indian J. Chem., 28B(12), pp. 1065–1068 (1989).
Yamada et al., Agr. Biol. Chem., 36(1), pp. 106–111 (1972).
Katritzky et al. (eds.), Best Synthetic Methods, Academic Press, London, pp. 105–134 (1996).
MacDougald et al., Current Biology, vol. 5, pp. 618–621 (1995).
Keller et al., Trends Endocrin. Metab., 4, pp. 291–296 (1993).
Gribble, J. Chem. Soc., Perkin I, pp. 1045–1075 (2000).
Bos et al., European Journal of Medicinal Chemistry, vol. 32, No. 3, 1997, pp. 253–261, XP004075426.
Grinev et al., Pharm. Chem. J., vol. 18, No. 2, 1984, pp. 94–98, XP001084869.
Andreeva et al., Pharm. Chem. J., vol. 30, No. 7, 1996, pp. 432–440, XP001084868.
Abstract corresponding to EP 0 572 863 (B1).
Gupta Y K et al., Indian Journal of Pharmacology, 1994, pp. 94–107, vol. 26, No. 2.

* cited by examiner

*Primary Examiner*—Emily Bernhardt
(74) *Attorney, Agent, or Firm*—George W. Johnston; Dennis P. Tramaloni; Samuel H. Megerditchian

(57) ABSTRACT

The present invention provides piperazine derivatives in accordance with formula (I)

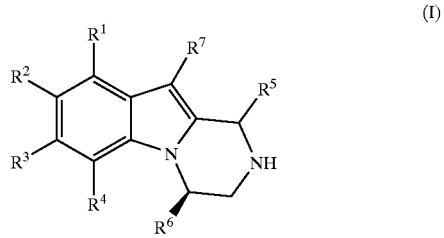

(I)

as well as salts, hydrates and esters thereof. The substituent designations are as provided in the specification. The compounds of the present invention can be used in the treatment of type II diabetes or obesity.

41 Claims, No Drawings

PIPERAZINE DERIVATIVES

FIELD OF THE INVENTION

The present invention relates to new piperazine derivatives, to processes and intermediates for their preparation, to pharmaceutical compositions containing them and to their medicinal use. The active compounds of the present invention are useful in treating obesity and other disorders.

BACKGROUND OF THE INVENTION

It has been recognised that obesity is a disease process influenced by environmental factors in which the traditional weight loss methods of dieting and exercise need to be supplemented by therapeutic products (S. Parker, *"Obesity: Trends and Treatments"*, Scrip Reports, PJB Publications Ltd, 1996).

Whether someone is classified as overweight or obese is generally determined on the basis of their body mass index (BMI), which is calculated by dividing body weight (kg) by height squared ($m^2$). Thus, the units of BMI are $kg/m^2$ and it is possible to calculate the BMI range associated with minimum mortality in each decade of life. Overweight is defined as a BMI in the range 25–30 $kg/m^2$, and obesity as a BMI greater than 30 $kg/m^2$. There are problems with this definition in that it does not take into account the proportion of body mass that is muscle in relation to fat (adipose tissue). To account for this, obesity can also be defined on the basis of body fat content: greater than 25% and 30% in males and females, respectively.

As the BMI increases there is an increased risk of death from a variety of causes that is independent of other risk factors. The most common diseases with obesity are cardiovascular disease (particularly hypertension), diabetes, particularly type II diabetes, (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (XENICAL®) and Sibutramine. Orlistat (a lipase inhibitor) inhibits fat absorption directly and tends to produce a high incidence of unpleasant (though relatively harmless) side-effects such as diarrhoea. Sibutramine (a mixed 5-HT/noradrenaline reuptake inhibitor) can increase blood pressure and heart rate in some patients. The serotonin releaser/reuptake inhibitors fenfluramine (Pondimin®) and dexfenfluramine (ReduX™) have been reported to decrease food intake and body weight over a prolonged period (greater than 6 months). However, both products were withdrawn after reports of preliminary evidence of heart valve abnormalities associated with their use. There is therefore a need for the development of a safer anti-obesity agent.

The non-selective $5\text{-HT}_{2C}$ receptor agonists/partial agonists m-chlorophenylpiperazine (mCPP) and trifluoromethylphenylpiperazine (TFMPP) have been shown to reduce food intake in rats (G. A. Kennett and G. Curzon, *Psychopharmacol.*, 1988, 96, 93–100; G. A. Kennett, C. T. Dourish and G. Curzon, *Eur. J. Pharmacol.*, 1987, 141, 429–435) and to accelerate the appearance of the behavioural satiety sequence (S. J. Kitchener and C. T. Dourish, *Psychopharmacol.*, 1994, 113, 369–377). Recent findings from studies with mCPP in normal human volunteers and obese subjects have also shown decreases in food intake. Thus, a single dose of mCPP decreased food intake in female volunteers (A. E. S. Walsh et al., *Psychopharmacol.*, 1994, 116, 120–122) and decreased the appetite and body weight of obese male and female subjects during subchronic treatment for a 14 day period (P. A. Sargeant et al., *Psychopharmacol.*, 1997, 133, 309–312). The anorectic action of mCPP is absent in $5\text{-HT}_{2C}$ receptor knockout mutant mice (L. H. Tecott et al., *Nature*, 1995, 374, 542–546) and is antagonised by the $5\text{-HT}_{2C}$ receptor antagonist SB-242084 in rats (G. A. Kennett et al., *Neuropharmacol.*, 1997, 36, 609–620). It seems therefore that mCPP decreases food intake via an agonist action at the $5\text{-HT}_{2C}$ receptor.

Other compounds which have been proposed as antidepressants and antibiotics, e.g. 1,2,3,4 include 1,2,3,4-tetrahydroppyrazino[1,2-a]indoles and ethyl 1-(2-aminoethyl)indole-2-carboxylates (Rajur et al. (1989) Indian J. Chem., 28B(12), 1065–1068), tricyclic pyrazidole analogs (Grinev et al. (1984), Khim. Farm.Zh. 18(2), 159–163), derivates of 1-methylamino-9-methyl-1,2,3,4-tetrahydrocarbazole (Andreeva et al. (1976), Khim.Farm.Zh., 10(11), 46–49), and mitomycin analogues (Yamada et al. (1972), Agr. Biol. Chem., 36(1), 106–111) are structurally different. Further, U.S. Pat. No. 3,317,524 discloses structurally different 1,2,3,4-tetrahydro-pyrazino[1,2-a]indoles as anti-inflammatory agents, as central nervous system depressants, as analgesics and as anti-convulsants.

Diabetes is a disease in which a patient's ability to control glucose levels in blood is impaired, because the ability to respond properly to the action of insulin has been partially lost. In type II diabetes, often referred to as non-insulin dependent diabetes mellitus (NIDDM), which afflicts 80–90% of all diabetic patients in developed countries, the Islets of Langerhans in the pancreas still produce insulin. However, the target organs, mainly muscle, liver and adipose tissue, exhibit a profound resistance to insulin stimulation, thus the body compensates by producing abnormally high levels of insulin. In the later stages of the disease, however, insulin secretion decreases due to pancreas exhaustion.

Current first line treatment for diabetes generally involves adoption of a diet low in fat and glucose and taking regular exercise. However, compliance can be moderate and as the disease progresses, treatment with hypoglycemic drugs, e.g. sulfonylureas or metformin, becomes necessary. A promising new class of drugs has recently been introduced that resensitize patients to their own insulin (insulin sensitizers), thereby reverting blood glucose and triglyceride levels to normal, and thus abolishing, or at least reducing, the requirement for exogenous insulin. Troglitazone (Resulin™) and rosiglitazone (Avandia™) belong to the thiazolidinediones (TZD) class of PPARγ-agonists and were the first representatives of the class approved for NIDDM treatment in several countries. These compounds, however, suffer from side effects including rare but severe liver toxicity (as seen with troglitazone), and increased body weight in humans. Therefore, new, better and more efficacious drugs for the treatment of conditions involving hyperglycemia, particularly NIDDM are urgently needed. Recent studies provided evidence that coagonism of PPARα and PPARγ would result in compounds with enhanced therapeutic potential, i.e. with an improved lipid profile effect on top of the normalization of glucose- and insulin-levels (Keller and Wahli: Trends Endocrin. Metab. 1993; 4:291–296, Macdonald and Lane: Current Biology Vol.5 pp.618–621 (1995)).

It is an object of this invention to provide selective, directly acting $5HT_2$ receptor ligands for use in therapy and particularly for use as anti-obesity agents. It is a further object of this invention to provide directly acting ligands selective for 5-HT$_{2B}$ and/or 5-HT$_{2C}$ receptors, for use in therapy and particularly for use as anti-obesity agents. It is a further object of this invention to provide selective, directly acting 5-HT$_{2C}$ receptor ligands, preferably 5-HT$_{2C}$ receptor agonists, for use in therapy and particularly for use as anti-obesity agents.

SUMMARY OF THE INVENTION

The invention is concerned with compounds of formula I and their pharmaceutically acceptable salts, solvates and esters

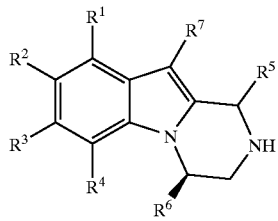

wherein

R$^1$, R$^2$, R$^3$ and R$^4$ are independently selected from hydrogen, halogen, hydroxy, alkyl, cycloalkyl, arylalkyl, aryl, alkoxy, alkoxyalkyl, haloalkyl, haloalkoxy, aryloxy, alkylcarbonyl, arylcarbonyl, alkylthio, arylthio, alkylsulfoxyl, arylsulfoxyl, alkylsulfonyl, arylsulfonyl, amino, nitro, cyano, alkoxycarbonyl, aryloxycarbonyl, mono- and di-alkylaminocarbonyl, alkylcarbonylamino, carboxy and heterocyclyl, or R$^3$ and R$^4$ form together a —CH$_2$—CH$_2$—CH$_2$—group;

with the proviso that at least one of the moieties R$^1$, R$^2$, R$^3$ and R$^4$ is not hydrogen;

R$^5$ is hydrogen, alkyl or cycloalkyl;

R$^6$ is hydrogen, alkyl, cycloalkyl, hydroxyalkyl or alkoxyalkyl; and

R$^7$ is hydrogen, halogen, alkyl, cycloalkyl, hydroxyalkyl, carboxyalkyl, carbamoylalkyl, alkoxycarbonylalkyl, aryloxycarbonylalkyl, formyl, alkylcarbonyl, alkoxy or alkylthio.

The compounds of formula (I) are ligands of 5HT$_2$ receptors and are useful in therapy, particularly for use as anti-obesity agents. The novel compounds of the present invention can also be used as efficacious drugs for the treatment and prevention of diabetes, particularly of non-insulin dependent diabetes mellitus.

DETAILED DESCRIPTION OF THE INVENTION

Compounds of formula (I) and their pharmaceutically acceptable salts, solvates and esters are useful ligands of 5HT$_2$ receptors:

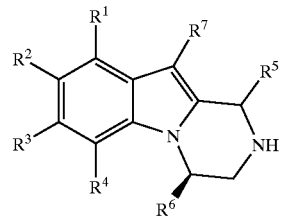

wherein

R$^1$, R$^2$, R$^3$ and R$^4$ are independently selected from hydrogen, halogen, hydroxy, alkyl, cycloalkyl, arylalkyl, aryl, alkoxy, alkoxyalkyl, haloalkyl, haloalkoxy, aryloxy, alkylcarbonyl, arylcarbonyl, alkylthio, arylthio, alkylsulfoxyl, arylsulfoxyl, alkylsulfonyl, arylsulfonyl, amino, nitro, cyano, alkoxycarbonyl, aryloxycarbonyl, mono- and di-alkylaminocarbonyl, alkylcarbonylamino, carboxy and heterocyclyl, or R$^3$ and R$^4$ form together a —CH$_2$—CH$_2$—CH$_2$— group; with the proviso that at least one of the moieties R$^1$, R$^2$, R$^3$ and R$^4$ is not hydrogen;

R$^5$ is hydrogen, alkyl or cycloalkyl;

R$^6$ is hydrogen, alkyl, cycloalkyl, hydroxyalkyl or alkoxyalkyl; and

R$^7$ is hydrogen, halogen, alkyl, cycloalkyl, hydroxyalkyl, carboxyalkyl, carbamoylalkyl, alkoxycarbonylalkyl, aryloxycarbonylalkyl, formyl, alkylcarbonyl, alkoxy or alkylthio.

The compounds of formula (I) are also useful in the treatment and/or prevention of disorders involving elevated plasma blood glucose, particularly diabetes mellitus (including Type II or non-insulin dependent diabetes mellitus (NIDDM); Type I or insulin dependent diabetes mellitus (IDDM); and Type III or malnutrition-related diabetes). The diabetes may be diabetes secondary to pancreatic disease; or diabetes related to steroid use. The compounds of formula (I) are also useful in the treatment and/or prevention of the sequelae of hyperglycaemia; in the treatment and/or prevention of diabetic complications; and in the treatment of insulin dependence.

The invention is of particular use in the treatment or prevention of diabetes mellitus (including Type II or non-insulin dependent diabetes mellitus (NIDDM); Type I or insulin dependent diabetes mellitus (IDDM); and Type III or malnutrition-related diabetes), and particularly in the treatment or prevention of Type II diabetes.

The present invention encompasses the use of compounds according to formula I for the acute and/or chronic treatment and/or prevention of disorders involving elevated plasma blood glucose, particularly the acute and/or chronic treatment of disorders involving elevated plasma blood glucose, and especially acute treatment of disorders involving elevated plasma blood glucose.

In the present description the term "alkyl", alone or in combination, signifies a straight-chain or branched-chain alkyl group with 1 to 8 carbon atoms, preferably a straight or branched-chain alkyl group with 1–4 carbon atoms. Examples of straight-chain and branched C$_1$-C$_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl, ethyl, propyl and isopropyl. Particularly preferred are methyl and ethyl.

The term "cycloalkyl", alone or in combination, signifies a cycloalkyl ring with 3 to 8 carbon atoms and preferably a cycloalkyl ring with 3 to 6 carbon atoms. Examples of $C_3$-$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methylcyclohexyl, dimethyl-cyclohexyl, cycloheptyl and cyclooctyl, preferably cyclopropyl and particularly cyclopentyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec.butoxy and tert.butoxy, preferably methoxy and ethoxy.

The term "alkoxycarbonyl" refers to a group of the formula alkoxy-C(O)—, wherein the term "alkoxy" is as defined above.

The term "alkoxycarbonylalkyl" refers to a group of the formula alkoxy-C(O)-alkyl, wherein the terms "alkoxy" and "alkyl" are as defined above.

The term "aryloxy", alone or in combination, signifies a group of the formula aryl-O— in which the term "aryl" has the previously given significance. Phenyloxy is an example of such an aryloxy group.

The term "aryloxycarbonyl", alone or in combination, refers to a group of the formula aryloxy-C(O)—, wherein the term "aroxy" is as defined above.

The term "haloalkyl", alone or in combination, signifies an allyl group as previously defined, wherein one or several hydrogen atoms, preferably one, two or three hydrogen atom(s) have/has been replaced by halogen. Examples of haloalkyl groups are trifluoromethyl, pentafluoromethyl and trichloromethyl. Preferred examples are trifluoromethyl and difluoromethyl.

The term "haloalkoxy", alone or in combination, signifies an alkoxy group as previously defined, wherein one or several hydrogen atoms, preferably one, two or three hydrogen atom(s) have/has been replaced by halogen. Examples of haloalkoxy groups are trifluoromethoxy, difluoromethoxy and trichloromethoxy.

The term "hydroxyalkyl", alone or in combination, signifies an alkyl group as defined above, wherein one or several hydrogen atoms, preferably one, have/has been replaced by hydroxy. Preferred is hydroxymethyl.

The term "alkoxyalkyl", alone or in combination, signifies an alkyl group as defined above, wherein one or several hydrogen atoms, preferably one, have/has been replaced by an alkoxy group as previously defined.

The term "carbonyl", alone or in combination, refers to a group of the formula —C(O).

The terms "alkylcarbonyl" or "alkanoyl", alone or in combination, refer to a group of the formula alkyl-C(O)— with alkyl as defined above.

The term "alkylthio", alone or in combination, signifies a group of the formula alkyl-S-in which the term "alkyl" has the previously given significance, such as methylthio, ethylthio, n-propylthio, isopropylthio. Preferred are methylthio and ethylthio.

The term "arylthio", alone or in combination, signifies a group of the formula aryl-S-in which the term "aryl" has the previously given significance. Phenylthio is an example of such an arylthio group.

The term "sulphonyl", alone or in combination, signifies a group of the formula $S(O)_2$—.

The term "sulfoxyl", alone or in combination, signifies a group of the formula S(O)—.

The term "aryl", alone or in combination, signifies a phenyl group which optionally carries one to three substituents each independently selected from alkyl, alkoxy, halogen, carboxy, alkoxycarbonyl, aminocarbonyl, hydroxy, amino, nitro and the like, such as phenyl, p-tolyl, 4-methoxyphenyl, 4-tert.butoxyphenyl, 4-fluorophenyl, 2-chlorophenyl, 3-chlorophenyl, 4-chlorophenyl, 4-hydroxyphenyl, 1-naphthyl and 2-naphthyl. Preferred is phenyl.

The term "heterocyclyl", alone or in combination, signifies a saturated, partially unsaturated or aromatic 5- to 10-membered heterocycle, preferably a 5- or 6-membered ring which contains one to three hetero atoms selected from nitrogen, oxygen and sulphur. If desired, it can be substituted on one to three carbon atoms by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl or on a tertiary nitrogen atom (i.e. =N—) by oxido, with halogen, alkyl, cycloalkyl and alkoxy being preferred. Examples of such heterocyclyl groups are pyrrolidinyl, piperidinyl, piperazinyl, morpholinyl, thiomorpholinyl, pyrazoyl, imidazoyl (e.g. imidazol-4-yl and 1-benzyloxycarbonyl-imidazol-4-yl), pyrazoyl, pyridyl, pyrazinyl, pyrimidinyl, hexahydro-pyrimidinyl, furyl, thienyl, thiazolyl, oxazolyl, indolyl (e.g. 2-indolyl), quinolyl (e.g. 2-quinolyl, 3-quinolyl and 1-oxido-2-quinolyl), isoquinolyl (e.g. 1-isoquinolyl and 3-isoquinolyl), tetrahydroquinolyl (e.g. 1,2,3,4-tetrahydro-2-quinolyl), 1,2,3,4-tetrahydroisoquinolyl (e.g. 1,2,3,4-tetrahydro-1-oxo-isoquinolyl) and quinoxalinyl.

The term "amino", alone or in combination, refers to the group —$NH_2$.

The term "halogen" or "halo" signifies fluorine, chlorine, bromine or iodine and preferably fluorine, chlorine or bromine and particularly fluorine and chlorine.

The term "carboxy", alone or in combination, signifies a —COOH group.

The term "carboxyalkyl" alone or in combination, signifies an alkyl group as previously described in which one hydrogen atom has been replaced by a carboxy group. The carboxymethyl group is preferred and particularly carboxyethyl.

The term "carbamoyl" refers to a group of the formula $NH_2$—C(O)—.

The term "carbamoylalkyl" refers to the group $NH_2$—C (O)-.alkyl, wherein the term "alkyl" is as defined above.

The term "formyl" refers to the group —CH=O.

The term "cyano", alone or in combination, signifies a group of the formula —CN.

Examples of pharmaceutically acceptable salts of the compounds of formula I are salts with physiologically compatible mineral acids such hydrochloric acid, sulphuric acid or phosphoric acid; or with organic acids such as methanesulphonic acid, acetic acid, trifluoroacetic acid, citric acid, fumaric acid, maleic acid, tartaric acid, succinic acid or salicylic acid. The compounds of formula I with free carboxy groups can also form salts with physiologically compatible bases. Examples of such salts are alkali metal, alkali earth metal, ammonium and alkylammonium salts such as the Na, K, Ca or tertramethylammonium salt. The compound of formula I can also be present in the form of zwitterions. Preferred examples of pharmaceutically acceptable salts ate hydrochloride salts and oxalate sals.

The invention expressly includes pharmaceutically acceptable derivatives of the compounds of formula I, particularly pharmaceutically acceptable esters of formula I. For example, the COOH groups in $R^1$ to $R^4$ or $R^6$ can be esterified. The alkyl and aralkyl esters are examples of acceptable esters. The methyl, ethyl, propyl, butyl and benzyl esters are preferred esters. The methyl and ethyl esters are especially preferred.

The compounds of formula I can also be solvated, e.g. hydrated. The solvation can be effected in the course of the manufacturing process or can take place e.g. as a consequence of hygroscopic properties of an initially anhydrous compound of formula I (hydration).

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

The compounds of formula I can contain several asymmetric centres and can be present in the form of optically pure enantiomers, mixtures of enantiomers such as, for example, racemates, optically pure diastercoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant).

The term "asymmetric carbon atom (C*)" means a carbon atom with four different substituents. According to the Cahn-Ingold-Prelog-Convention the asymmetric carbon atom can be of the "R" or "S" configuration.

Preferred are chiral compounds of formula (I),

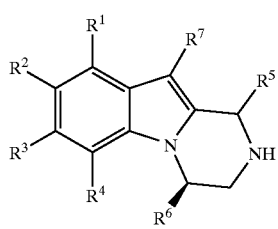

(I)

wherein $R^1$ to $R^7$ are defined as before. Formula (I) means that the asymmetric carbon atom

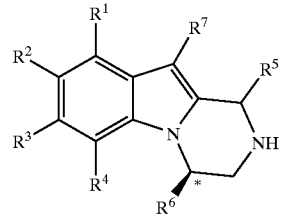

(I)

is of the R or the S configuration. Particularly preferred are chiral compounds of formula (I), wherein C* is of the R configuration and $R^1$ to $R^7$ are defined as before. Further particularly preferred compounds of formula (I) are those, wherein C* is of the R configuration and wherein $R^6$ means hydrogen, alkyl or cycloalkyl and $R^1$ to $R^5$ and $R^7$ are defined as before.

Further preferred are those compounds according to formula (I), wherein C* is of the S configuration and $R^6$ means alkoxymethyl or preferably hydroxymethyl and $R^1$ to $R^5$ and $R^7$ are defined as before.

Most preferred are chiral compounds of formula (I), wherein Ce is of the R configuration and $R^1$ to $R^7$ are defined as before with the proviso that in case $R^6$ means alkoxymethyl or preferably hydroxymethyl the S configuration of C* is preferred. In the preferred cases the $R^6$ substituent occupies an equivalent stereochemical position in the 3-dimensional space.

Preferred are compounds according to formula I, wherein $R^1$ to $R^7$ are defined as before and their pharmaceutically acceptable salts and esters.

Preferred are compounds according to formula I

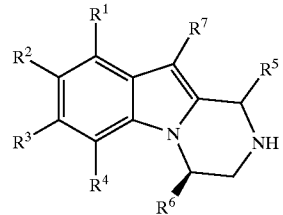

(I)

wherein
$R^1$, $R^2$, $R^3$ and $R^4$ are independently selected from hydrogen, halogen, hydroxy, alkyl, cycloalkyl, arylalkyl, aryl, alkoxy, alkoxyalkyl, haloalkyl, haloalkoxy, aryloxy, alkylcarbonyl, arylcarbonyl, alkylthio, arylthio, alkylsulfoxyl, arylsulfoxyl, alkylsulfonyl, arylsulfonyl, amino, nitro, cyano, alkoxycarbonyl, aryloxycarbonyl, mono- and di-alkylaminocarbonyl, alkylcarbonylamino, carboxy or heterocyclyl; with the proviso that at least one of the moieties
$R^1$, $R^2$, $R^3$ and $R^4$ is not hydrogen.
$R^5$ is hydrogen, alkyl or cycloalkyl;
$R^6$ is alkyl or cycloalkyl;
$R^7$ is hydrogen, halogen, alkyl, cycloalkyl, hydroxyalkyl, carboxyalkyl, carbamoylalkyl, alkoxycarbonylalkyl, aryloxycarbonylalkyl, formyl, alkylcarbonyl, alkoxy or alkylthio;
and their pharmaceutically acceptable salts, solvates and esters.

A preferred embodiment of the present invention refers to the above compounds, wherein $R^1$, $R^2$, $R^3$ and $R^4$ are independently selected from hydrogen, halogen, alkyl, alkoxy, haloalkoxy or haloalkyl.

In another embodiment, the above compounds are characterized in $R^1$, $R^2$, $R^3$ or $R^4$ are independently selected from hydrogen, halogen, alkyl, e.g. methyl and ethyl, alkoxy, e.g. methoxy, halomethyl, and halomethoxy, more preferably from hydrogen chloro, fluoro, bromo, trifluoromethyl, methyl, ethyl, methoxy and trifluoromethoxy.

Preferred are compound according to formula I, wherein $R^1$, $R^2$, $R^3$ and $R^4$ are independently selected from hydrogen, halogen, alkyl, haloalkyl, haloalkoxy and cyano or $R^3$ and $R^4$ form together a —$CH_2$—$CH_2$—$CH_2$— group.

Further preferred are compounds of formula I, wherein $R^1$, $R^2$, $R^3$ and $R^4$ are independently selected from hydrogen, halogen, alkyl, trifluoromethyl and cyano. Particularly preferred compounds of formula I are those, wherein $R^1$, $R^2$, $R^3$ and $R^4$ are independently selected from hydrogen, methyl, ethyl, fluoro, chloro, cyano and trifluoromethyl.

Also preferred are compounds of formula 1, wherein $R^4$ is methyl or ethyl and $R^1$, $R^2$ and $R^3$ are hydrogen.

Further particularly preferred are compounds according to formula I, wherein $R^4$ is fluoro, cyano or trifluoromethyl and $R^1$, $R^2$ and $R^3$ are independently selected from hydrogen or methyl.

Preferably, $R^5$ in the above compounds is hydrogen or alkyl, more preferably hydrogen or methyl, and most preferably hydrogen.

In a further preferred embodiment, the above compounds are characterized in that $R^6$ is alkyl or cycloalkyl, preferably alkyl, more preferably methyl or ethyl. Further preferred are compounds of formula I, wherein $R^6$ is alkyl or hydroxyalkyl. Particularly preferred are compounds of formula I, wherein $R^6$ is methyl.

In another preferred embodiment, the above compounds are characterized in that $R^7$ is hydrogen, alkyl or alkoxy, more preferably hydrogen, methyl or methoxy, even more preferably hydrogen or methyl and most preferably $R^7$ is hydrogen.

The preferred compounds of formula (I) may be selected from the group consisting of:

(R)-6-ethyl-4-methyl-1,2,3,4-tetrahydro-pyrazino[1,2-a]indole;
(R)-4-methyl-7-trifluoromethyl-1,2,3,4-tetrahydro-pyrazino[1,2-a]indole;
(R)-7-bromo-4-methyl-1,2,3,4-tetrahydro-pyrazino[1,2-a]indole;
(R)-9-chloro-4-methyl-1,2,3,4-tetrahydro-pyrazino[1,2-a]indole;
(R)-7-chloro-8-fluoro-4-methyl-1,2,3,4-tetrahydro-pyrazino[1,2-a]indole;
(R)-4,8-dimethyl-7-trifluoromethyl-1,2,3,4-tetrahydro-pyrazino[1,2-a]indole;
(R)-7,9-dichloro-4-methyl-1,2,3,4-tetrahydro-pyrazino[1,2-a]indole;
(R)-6,9-difluoro-4-methyl-1,2,3,4-tetrahydro-pyrazino[1,2-a]indole;
(R)-6-fluoro-4-methyl-1,2,3,4-tetrahydro-pyrazino[1,2-a]indole;
(R)-4,6-dimethyl-1,2,3,4-tetrahydro-pyrazino[1,2-a]indole;
(R)-8-fluoro-4-methyl-1,2,3,4-tetrahydro-pyrazino[1,2-a]indole;
(R)-7-bromo-9-fluoro-4-methyl-1,2,3,4-tetrahydro-pyrazino[1,2-a]indole;
(R)-7-chloro-10-methoxy-4-methyl-1,2,3,4-tetrahydro-pyrazino[1,2-a]indole;
(R)-7-chloro-4,6,10-trimethyl-1,2,3,4-tetrahydro-pyrazino[1,2-a]indole;
(R)-7-bromo-4-ethyl-1,2,3,4-tetrahydro-pyrazino[1,2-a]indole;
(R)-7-bromo-4-ethyl-1,2,3,4-tetrahydro-pyrazino[1,2-a]indole;
(R)-4-methyl-6-trifluoromethoxy-1,2,3,4-tetrahydro-pyrazino[1,2-a]indole;
(R)-7-chloro-4-ethyl-1,2,3,4-tetrahydro-pyrazino[1,2-a]indole;
(R)-4-methyl-7,9-bis-trifluoromethyl-1,2,3,4-tetrahydro-pyrazino[1,2-a]indole;
(R)-7-chloro-4-methyl-1,2,3,4-tetrahydro-pyrazino[1,2-a]indole;
(R)-4,6,9-trimethyl-1,2,3,4-tetrahydro-pyrazino[1,2-a]indole;
(R)-4,6,7-trimethyl-1,2,3,4-tetrahydro-pyrazino[1,2-a]indole;
(R)-7-chloro-4,6-dimethyl-1,2,3,4-tetrahydro-pyrazino[1,2-a]indole;
(R)-4,8-dimethyl-1,2,3,4-tetrahydro-pyrazino[1,2-a]indole;
(R)-8-fluoro-1-methyl-7-trifluoromethyl-1,2,3,4-tetrahydro-pyrazino[1,2-a]indole;
(R)-8-bromo-4,7-dimethyl-1,2,3,4-tetrahydro-pyrazino[1,2-a]indole;
(R)-4,7-dimethyl-1,2,3,4-tetrahydro-pyrazino[1,2-a]indole;
(R)-4,7,8-trimethyl-1,2,3,4-tetrahydro-pyrazino[1,2-a]indole;
(R)-7-chloro-4,8-dimethyl-1,2,3,4-tetrahydro-pyrazino[1,2-a]indole;
(R)-7,8-dichloro-4-methyl-1,2,3,4-tetrahydro-pyrazino[1,2-a]indole;
(R)-4-methyl-6-trifluoromethyl-1,2,3,4-tetrahydro-pyrazino[1,2-a]indole;
(R)-7-fluoro-4,6-dimethyl-1,2,3,4-tetrahydro-pyrazino[1,2-a]indole;
(R)-6-bromo-8-fluoro-4-methyl-1,2,3,4-tetrahydro-pyrazino[1,2-a]indole;
(R)-8-fluoro-4,6-dimethyl-1,2,3,4-tetrahydro-pyrazino[1,2-a]indole;
(R)-6-ethyl-8-fluoro-4-methyl-1,2,3,4-tetrahydro-pyrazino[1,2-a]indole;
(R)-7-chloro-4,10-dimethyl-1,2,3,4-tetrahydro-pyrazino[1,2-a]indole;
(R)-6,7-dichloro-4-methyl-1,2,3,4-tetrahydro-pyrazino[1,2-a]indole;
(R)-10-ethoxy-4,6-dimethyl-1,2,3,4-tetrahydro-pyrazino[1,2-a]indole;
(R)-10-methoxy-4,6-dimethyl-1,2,3,4-tetrahydro-pyrazino[1,2-a]indole;
(R)-4,7,9-trimethyl-1,2,3,4-tetrahydro-pyrazino[1,2-a]indole;
(R)-6-bromo-4-methyl-1,2,3,4-tetrahydro-pyrazino[1,2-a]indole;
(R)-8-fluoro-4,7-dimethyl-1,2,3,4-tetrahydro-pyrazino[1,2-a]indole;
(R)-6-fluoro-4,7-dimethyl-1,2,3,4-tetrahydro-pyrazino[11,2-a]indole;
(R)-4-methyl-1,2,3,4-tetrahydro-pyrazino[1,2-a]indole-6-carbonitrile;
(R)-6-chloro-4,8-dimethyl-1,2,3,4-tetrahydro-pyrazino[1,2-a]indole;
(R)-6-fluoro-4,9-dimethyl-1,2,3,4-tetrahydro-pyrazino[1,2-a]indole;
(R)-6-bromo-4,7-dimethyl-1,2,3,4-tetrahydro-pyrazino[1,2-a]indole;
(R)-6-chloro-4,7-dimethyl-1,2,3,4-tetrahydro-pyrazino[1,2-a]indole;
(R)-10-methyl-2,3,7,8,9,10-hexahydro-1H-8,10a-diaza-cyclopenta[c]fluorene;
(R)-7-bromo-4,6-dimethyl-1,2,3,4-tetrahydro-pyrazino[1,2-a]indole;

(R)-7-chloro-6-fluoro-4-methyl-1,2,3,4-tetrahydro-pyrazino [1,2-a]indole;
(R)-4,6,10-trimethyl-1,2,3,4-tetrahydro-pyrazino[1,2-a] indole;
(R)-8-bromo-7-fluoro-4-methyl-1,2,3,4-tetrahydro-pyrazino[1,2-a]indole;
(S)-(7-trifluoromethyl-1,2,3,4-tetrahydro-pyrazino[1,2-a] indol-4-yl)-methanol; and
(S)-(7-methyl-1,2,3,4-tetrahydro-pyrazino[1,2-a]indol-4-yl)-methanol.

The most preferred compound may be selected from the group consisting of:
(R)-6-ethyl-4-methyl-1,2,3,4-tetrahydro-pyrazino[1,2-a] indole;
(R)-4,6-dimethyl-1,2,3,4-tetrahydro-pyrazino[1,2-a]indole;
(R)-7-chloro-4-methyl-1,2,3,4-tetrahydro-pyrazino[1,2-a] indole;
(R)-4-methyl-6-trifluoromethyl-1,2,3,4-tetrahydro-pyrazino [1,2-a]indole;
(R)-6-ethyl-8-fluoro-4-methyl-1,2,3,4-tetrahydro-pyrazino [1,2-a]indole;
(R)-8-fluoro-4,7-dimethyl-1,2,3,4-tetrahydro-pyrazino[1,2-a]indole;
(R)-6-fluoro-4,7-dimethyl-1,2,3,4-tetrahydro-pyrazino[1,2-a]indole;
(R)-4-methyl-1,2,3,4-tetrahydro-pyrazino[1,2-a]indole-6-carbonitrile; and
(R)-4,6,10-trimethyl-1,2,3,4-tetrahydro-pyrazino[1,2-a] indole.

Further, processes for the manufacture of the compounds according to formula I are an object of the present invention. The substituents and indices used in the following schemes have the significance given above unless indicated to the contrary.

Scheme 1:

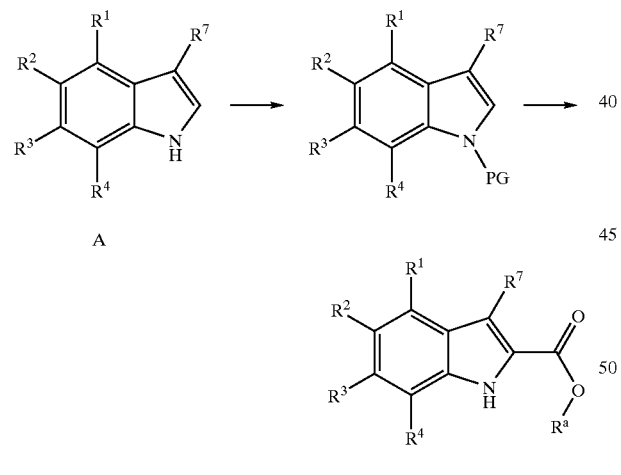

A

B

Indoles of formula A can be prepared by methods known in the art, (e.g., T. L. Gilchrist, "Heterocyclic Chemistry", 1997 or "The Chemistry of Heterocyclic Compounds" Vol. 25, 1972 or Joule, J. A. "Indoles, isoindoles, their reduced derivatives, and carbazoles". Rodd's Chem. Carbon Compd. 1997 or G. W. Gribble, J. Chem. Soc. Perkin 12000, 1045).

Indole-2-carboxylates of formula B can be prepared by methods known in the art (see above) or alternatively from indoles of formula A by first protecting the indole nitrogen with a suitable protecting group (PG; e.g., tert-butoxycarbonyl (Boc)), treating the protected indole derivative with a suitable base under anhydrous conditions (e.g., with lithium 2,2,6,6-tetramethylpiperidide in THF), reacting the intermediate anion with a chloroformate (e.g. ethyl chloroformate) and removing the protecting group (e.g., by treatment with acid for the Boc protecting group). $R^a$ in Scheme 1 is an alkyl group, preferably a lower alkyl group, preferably methyl or ethyl.

Scheme 2:

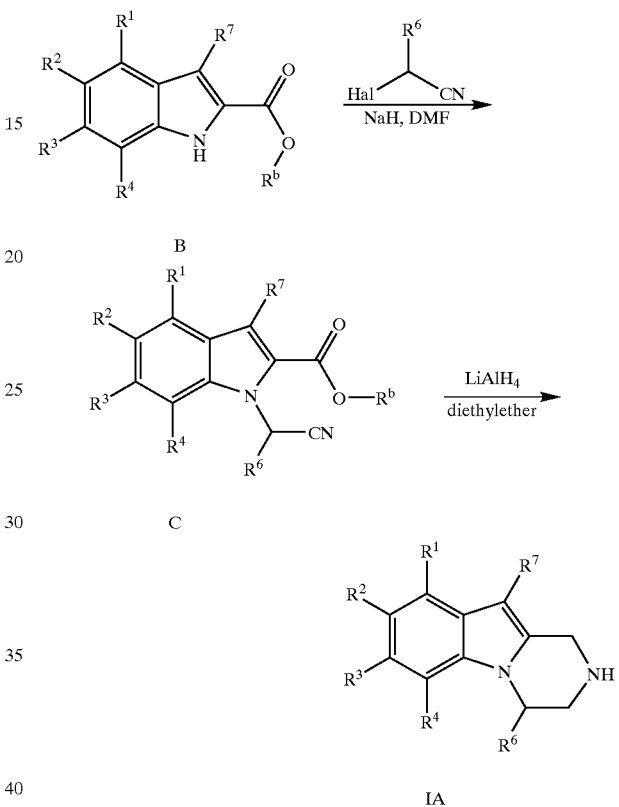

Tetrahydro-pyrazinoindoles of formula IA can be prepared by a process where the indole-2-carboxylate of formula B is first reacted with an alpha halo alkanenitrile (e.g., 2-bromo propionitrile) in a suitable solvent (e.g., DMF) with a suitable base (e.g., NaH). The intermediate C is reduced and cyclized to the tetrahydro-pyrazinoindole IA by reaction with a suitable reducing agent in a suitable solvent (e.g., LiAlH₄ in THF or diethylether). Rb in Scheme 2 is an alkyl group, preferably a lower alkyl group, preferably methyl or ethyl.

Scheme 3:

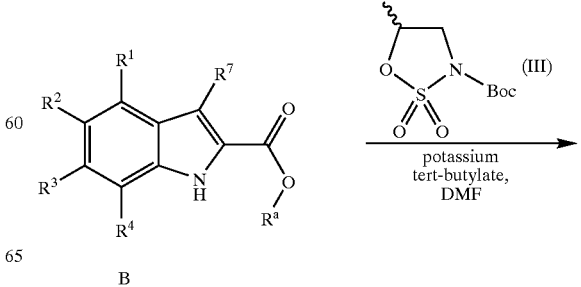

B

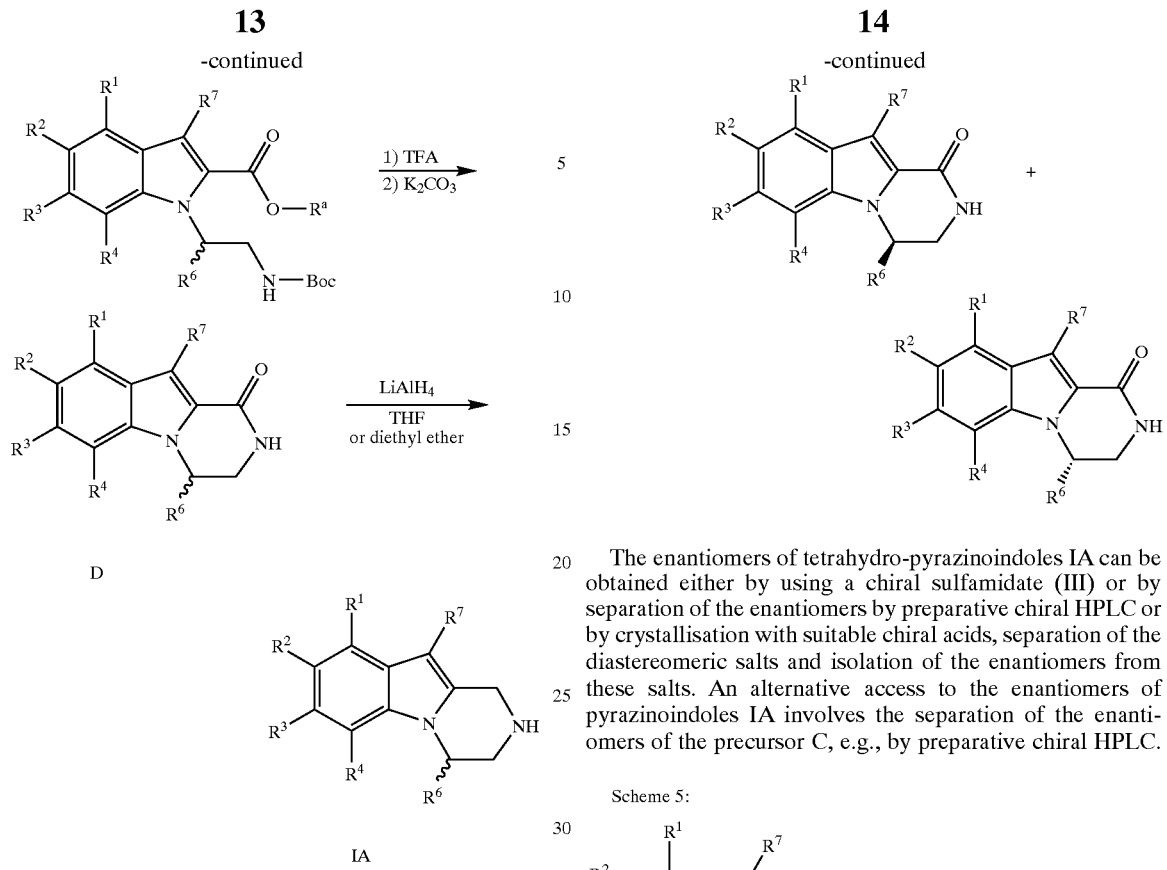

Tetrahydro-pyrazinoindoles of formula IA can also be prepared by a process where the indole-2-carboxylate of formula B is first reacted with the hitherto unknown Boc-sulfamidate (III) in a suitable solvent (e.g., DMF) with a suitable base (e.g., potassium tert-butylate or sodium hydride) followed by removal of the Boc protecting group and ring closure in the presence of base (e.g., potassium carbonate). The stereochemistry of the carbon atom attached to $R^6$ in Boc-sulfamidate III is inverted (>90% e.e.) in this reaction sequence. The intermediate amide (D) is reduced with a suitable reducing agent in a suitable solvent (e.g., LiAlH$_4$ in diethyl ether or borane-dimethylsulfide complex in THF). $R^a$ in Scheme 3 is an alkyl group, preferably a lower alkyl group, preferably methyl or ethyl.

If racemic Boc-sulfamidate III is used in this process, the enantiomers of intermediate D can be obtained, e.g., by preparative chiral HPLC as depicted in Scheme 4.

Scheme 4:

Scheme 4:

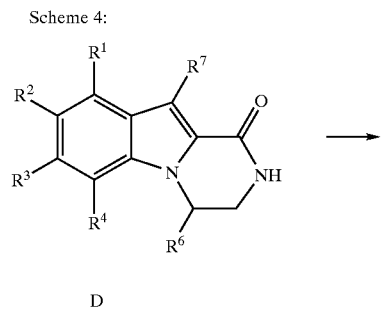

D

The enantiomers of tetrahydro-pyrazinoindoles IA can be obtained either by using a chiral sulfamidate (III) or by separation of the enantiomers by preparative chiral HPLC or by crystallisation with suitable chiral acids, separation of the diastereomeric salts and isolation of the enantiomers from these salts. An alternative access to the enantiomers of pyrazinoindoles IA involves the separation of the enantiomers of the precursor C, e.g., by preparative chiral HPLC.

Scheme 5:

Indole derivatives F can be prepared according to scheme 6, starting from protected o-iodoanilines (a suitable protective group, PG$^1$, is, e.g. N-methoxycarbonyl) by cross-coupling reaction with suitably substituted and optionally protected carbinols (preferred protective groups are silyl ethers, especially preferred is tert-butyl-dimethylsilyl). The reaction proceeds in the presence of a suitable catalyst (e.g., bis-triphenylphosphine palladium dichloride and copper(I) iodide as co-catalyst) in a suitable solvent (e.g. triethylamine). The intermediate is treated with a base (e.g.

Scheme 6:

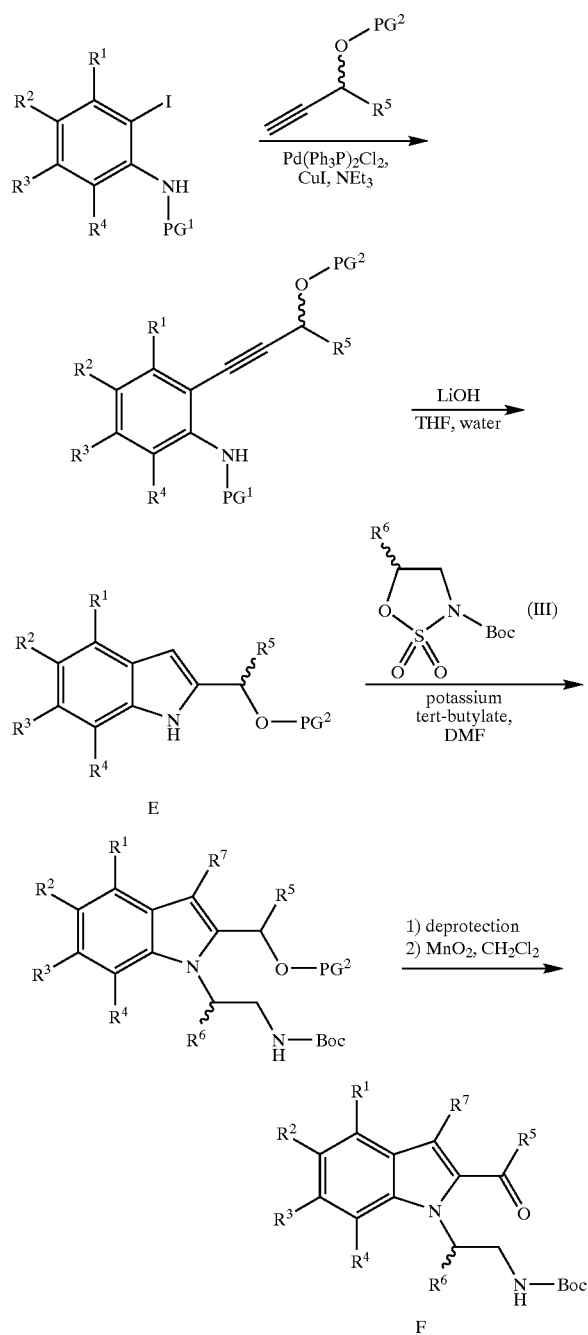

PG¹ and PG² are protectiong groups

Alkylation of E with the hitherto unknown Boc-sulfamidate (III) in a suitable solvent (e.g., DMF) in the presence of a suitable base (e.g., NaH or potassium tert-butylate), followed by deprotection of the alcohol (e.g., with tetrabutylammoniumfluoride) in a solvent (e.g., THF) and oxidation of the alcohol (e.g., with manganese dioxide in dichloromethane) leads to intermediate F. The stereochemistry of the carbon atom attached to $R^6$ in Boc-sulfamidate III is inverted (>90% e.e.) in this reaction sequence.

Scheme 7:

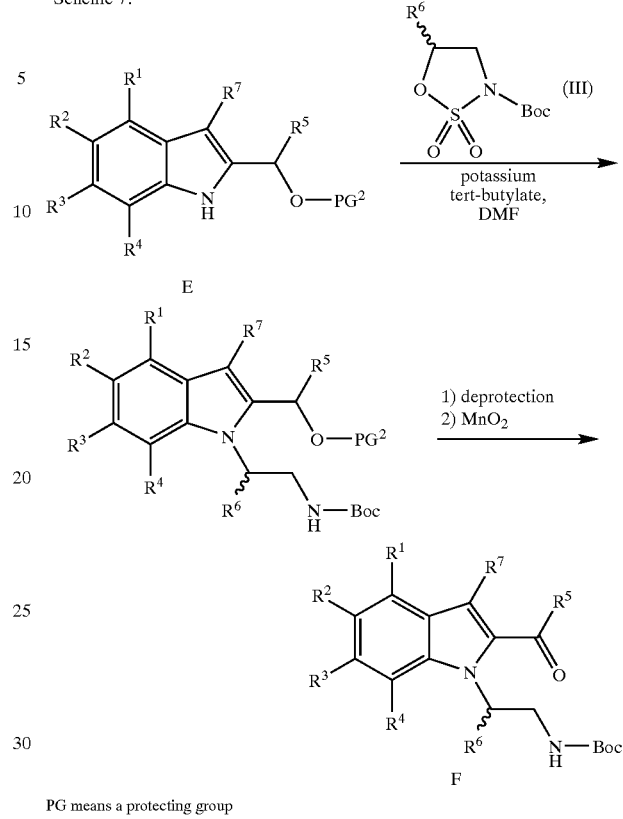

PG means a protecting group

Indole derivatives F can also be prepared according to scheme 7bis, starting from protected o-iodoanilines (a suitable protective group, PG¹, is, N-methoxycarbonyl) by cross-coupling reaction with propargyl alcohol derivatives in the presence of a suitable catalyst (e.g., bis-triphenylphosphine palladium dichloride and copper(I) iodide as co-catalyst) in a suitable solvent (e.g. triethylamine), followed by treatment with a base (e.g. LiOH in THF/water). The alcohol intermediate is oxidised, e.g., with manganese dioxide, to yield the indole derivative Z. Alkylation of Z with Boc-sulfamidate (III) in a suitable solvent (e.g., DMF) with a suitable base (e.g., potassium tert-butylate or NaH) leads to intermediate F. The stereochemistry of the carbon atom attached to $R^6$ in Boc-sulfamidate III is inverted (>90% e.g.) in this reaction.

Scheme 7bis

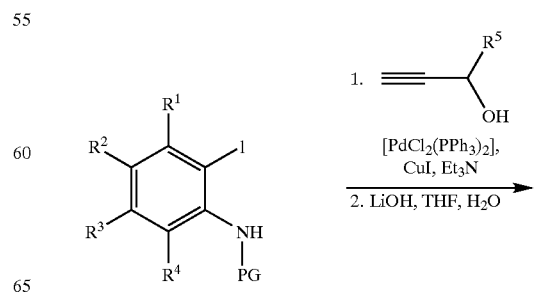

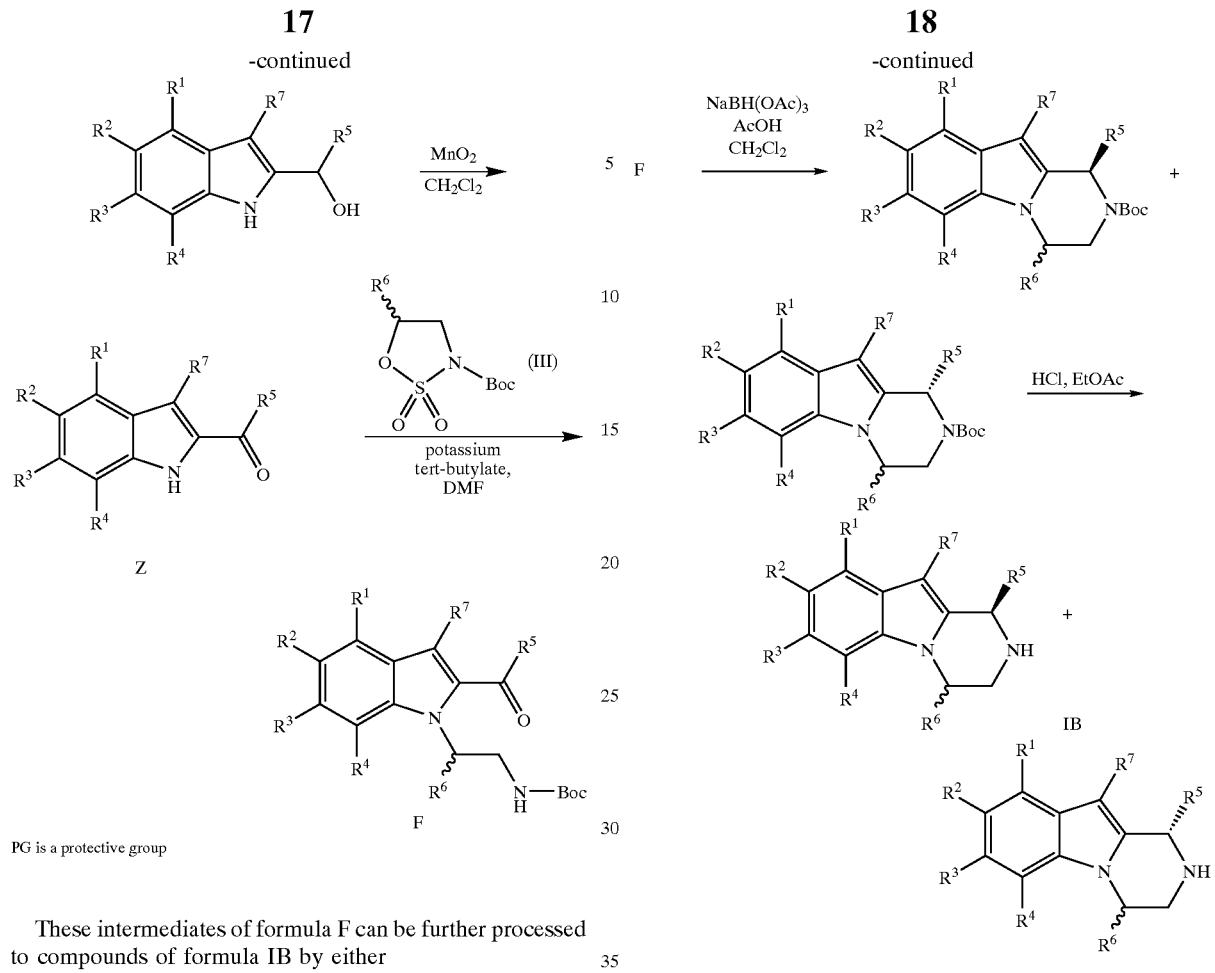

PG is a protective group

These intermediates of formula F can be further processed to compounds of formula IB by either

- removal of the Boc protecting group (e.g., with trifluoroacetic acid) to yield an imine intermediate which is not isolated but reduced directly with lithium aluminium hydride to yield IB as a separable mixture of epimers,
- or direct reductive amination (e.g., with sodium triacetoxyborohydride, molecular sieves and acetic acid in a suitable solvent, e.g., dichloromethane) followed by removal of the protecting group (e.g., with hydrochloric acid in ethyl acetate) as depicted in scheme 8.

Scheme 8

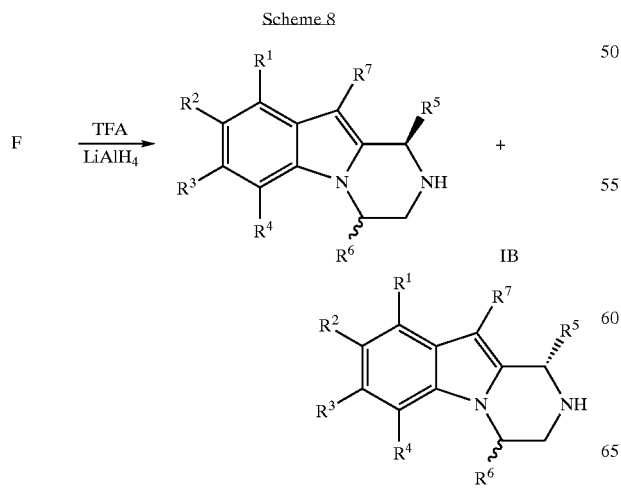

A variety of substituents $R^7$, preferably those functional groups that do not tolerate the methods described for the pyrazinoindole synthesis can be introduced starting from pyrazinoindole IC. To that end, the amine nitrogen of IC is protected, e.g., as the tert-butyl carbamate (protecting group PG) to generate compound G.

Scheme 9

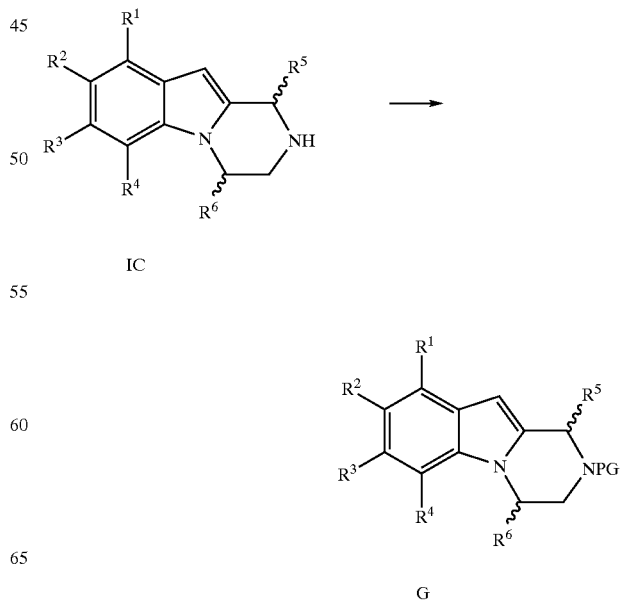

Several examples for the elaboration of compound G are highlighted in Schemes 10 and 11 (other substituents, $R^7$, can be introduced using methods known in the art (e.g., A. R Katritzky et al. (eds.), 'Indoles' (Best Synthetic Methods), Academic Press, London, 1996, pp. 105–134):

a) Vilsmeier reaction (DMF-POCl$_3$) yields aldehyde H, which can be further converted, e. g., into a1) alcohol derivative J (by reduction, e.g. with NaBH$_4$), which can be alkylated with a compound, $R^{20}$—X, to produce K ($R^{20}$ is alkyl, cycloalkyl, and X is a leaving group, preferably Br or I);

a2) olefin L (by e.g., treatment with a phosphorane, Ph$_3$P=CHR$^{21}$), where $R^{21}$ is H, alkyl, cycloalkyl, alkenyl, aryl);

a3) 10-methyl-tetrahydropyrazino[1,2-a]indole ID (by deprotection, e.g., with hydrogen chloride in ethyl acetate in the case of PG=Boc, followed by reduction, e.g., with triethylsilane);

a4) hydroxyimino and oxime M (by condensation with hydroxylamine or a hydroxylamine-O-ether respectively), which can be transformed into nitrile N, e.g., by treatment with trifluoroacetic anhydride; and a5) carboxylic acid derivative P by oxidation e.g. with sodium chlorite, optionally followed by esterification with alcohols, $R^{21}$OH.

Scheme 10

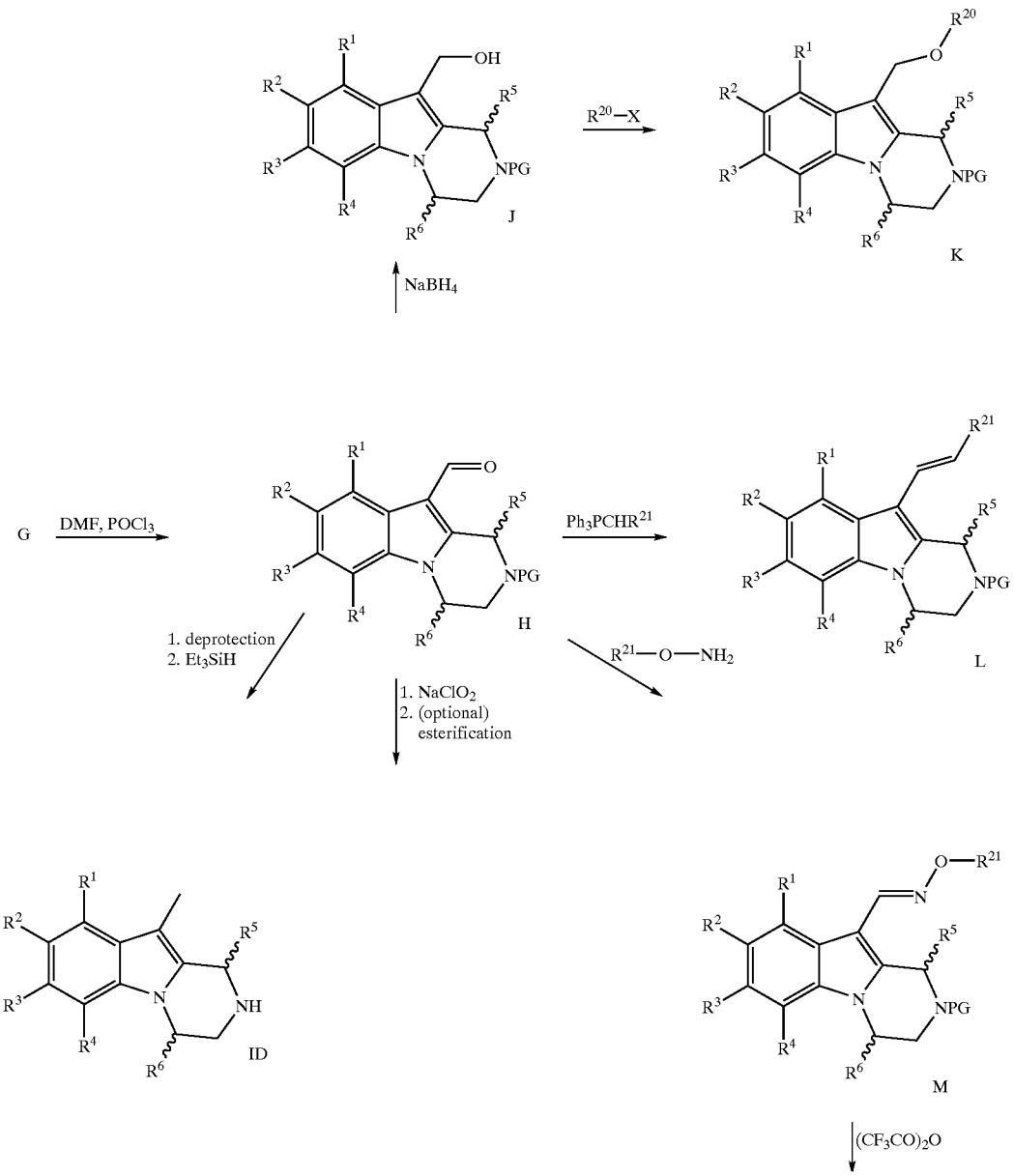

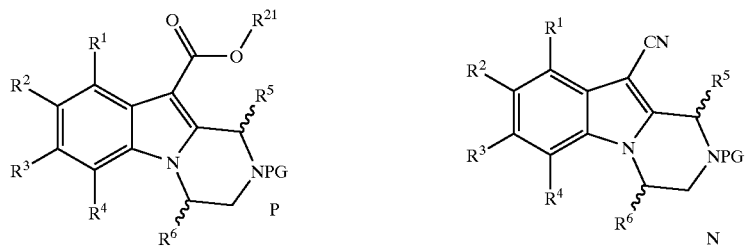

b) Halogenation (preferably with N-iodosuccinimide or N-bromosuccinimide in acetonitrile) yields halide Q, which can be further converted, e.g., into

- b1) compound R, by cross-coupling reaction ($R^{22}$=alkyl, aryl, alkenyl, alkynyl) using methods known in the art (e.g., F. Diederich, P. J. Stang (eds.), Metal-catalysed Cross-coupling Reactions, Wiley-VCH, 1998);
- b2) nitrile N, by reaction, e.g., with NaCN in the presence of [$(Ph_3P)_4Pd$] and CuI in acetonitrile), which can be elaborated, e.g., into carboxylic acid derivative, P; and
- b3) compound S, e.g., by cross-coupling reaction with bis(pinacolato)diboron in the presence of a palladium catalyst, e.g., [$PdCl_2(dppf)$], and a base, e.g., potassium acetate, followed by oxidation of the boronic acid intermediate with hydrogen peroxide.

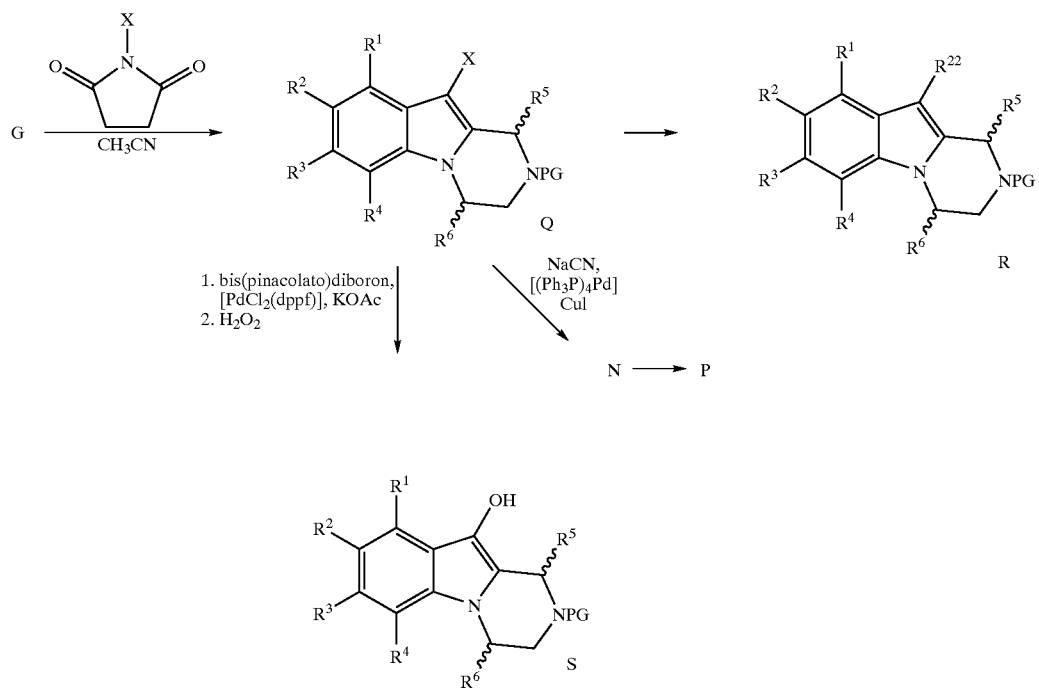

Scheme 11

Cleavage of the protective group in compounds H, J, K, L, M, N, P, Q, R, or S (e.g., with acid such as trifluoroacetic acid or hydrogen chloride in a suitable solvent such as ethyl acetate in the case of PG=Boc) yields tetrahydropyrazino[1,2-a]indoles IB.

Scheme 12

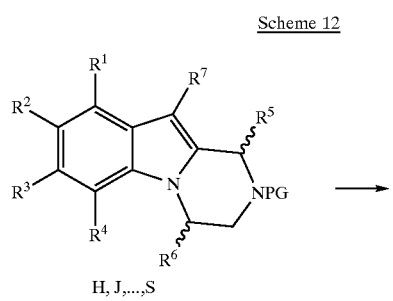

H, J,...,S

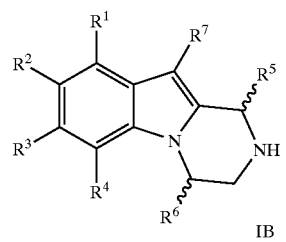

IB

Tetrahydropyrazino[1,2-a]indoles of formula IE can also be prepared as shown in Scheme 13. Amide T is halogenated (preferably with N-iodosuccinimide or N-bromosuccinimide in acetonitrile) to produce compound U, which is subjected to a cross-coupling reaction using methods known in the art (e.g., F. Diederich, P. J. Stang (eds.), Metal-catalyzed Cross-coupling Reactions, Wiley-VCH, 1988). Reduction of the cross-coupling product W (e.g., with LiAlH$_4$ in Et$_2$O) yields IE with R$^{22}$ defined as before.

Scheme 13

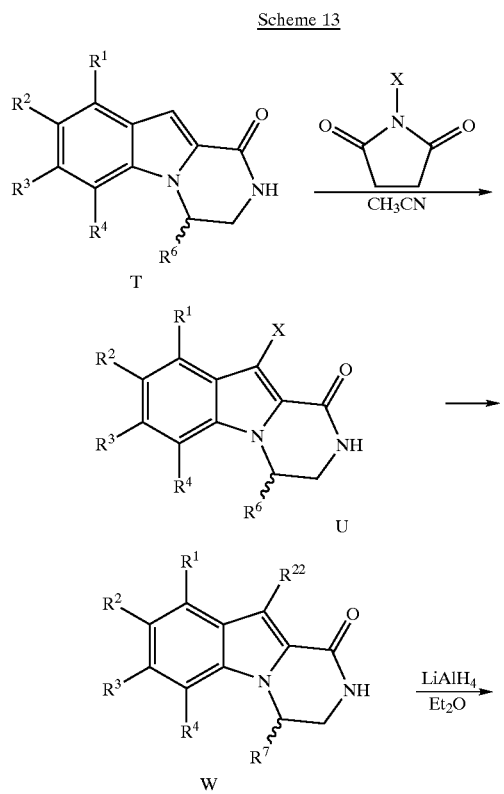

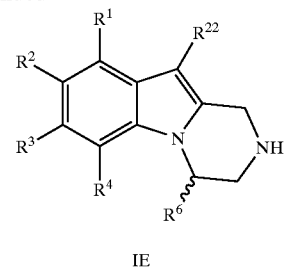

IE

Functional groups R$^1$ to R$^4$ that do not tolerate the methods described for the pyrazino-indole synthesis can be prepared from such functional groups that do by methods known in the art (e.g. March, Advanced Organic Chemistry 4$^{th}$ edition or Comprehensive Organic Functional Group Transformations, 1995).

Scheme 14

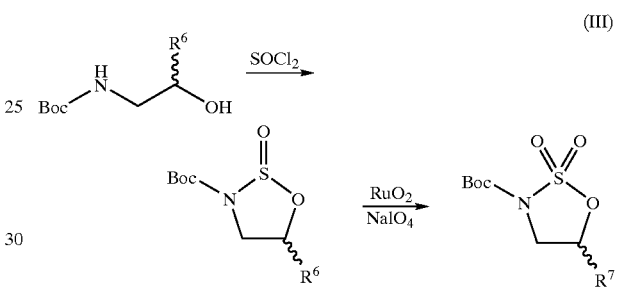

(III)

The hitherto unknown Boc-sulfamidate III can be prepared according to scheme 14 by treating Boc-protected ethanolamine derivatives with thionylchloride in a suitable solvent e.g. THF or ethyl acetate in the presence of a suitable base e.g. triethylamine or imidazole and oxidising the intermediate (e.g., with sodium metaperiodate and ruthenium (IV)oxide) in a suitable solvent (e.g., ethyl acetate). The stereochemistry of the carbon atom attached to R$^6$ remains unchanged (e.e. >97%) over this sequence.

The processes as described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base, an acid addition salt, particularly a pharmaceutically acceptable acid addition salt, may be obtained by dissolving the free base in a suitable organic solvent and treating the solution with an acid, in accordance with conventional procedures for preparing acid addition salts from basic compounds.

Another embodiment of the present invention relates to processes for the prepartion of compounds of formula (I) comprising comprising a reaction with a compound of formula (III)

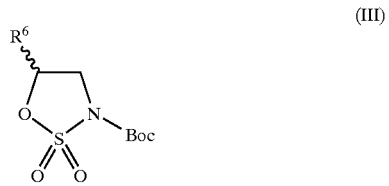

(III)

wherein $R^6$ is as defined above with a compound selected from the group consisting of

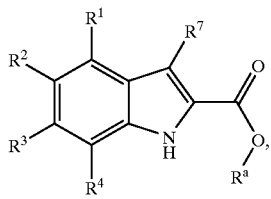

wherein $R^1$, $R^2$, $R^3$, $R^4$, and $R^7$ are as defined above and $R^a$ is alkyl; and b)

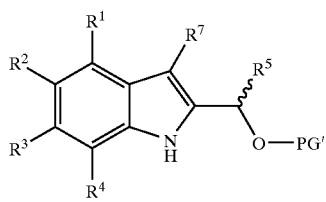

E wherein $R^1$, $R^2$, $R^3$, $R^4$, $R^5$, and $R^7$ are as defined above; and PG' is hydrogen or an OH-protecting group, e.g. trimethylsilyl, tert-butyldimethylsilyl, acetyl, methoxymethyl or 2-tetrahydropyranyl.

c)

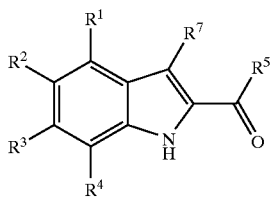

Z wherein $R^1$, $R^2$, $R^3$, $R^4$, $R^5$, and $R^7$ are as defined above;

Another preferred aspect of this invention relates to intermediates of formula (III)

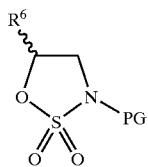

(III)

wherein $R^6$ is as defined above and PG is a nitrogen protecting group, e.g. BOC. Especially preferred embodiments of formula (III) are (S)-5-Methyl-2,2-dioxo-[1,2,3]oxathiazolidine-3-carboxylic acid tert-butyl ester and (R,S)-5-Ethyl-2,2-dioxo-[1,2,3]oxathiazolidine-3-carboxylic acid tert-butyl ester.

The compounds of formula (I) may be used in the treatment (including prophylactic treatment) of disorders associated with 5-HT$_2$ receptor function. The compounds may act as receptor agonists or antagonists. Preferably, the compounds maybe used in the treatment (including prophylactic treatment) of disorders associated with 5-HT$_{2B}$ and/or 5-HT$_{2C}$ receptor function. Preferably, the compounds may be used in the treatment (including prophylactic treatment) of disorders where a 5-HT$_{2C}$ receptor agonist is required.

The compounds of formula (I) maybe used in the treatment or prevention of central nervous disorders such as depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, obesity, bulimia, anorexia nervosa or premenstrual tension; damage of the central nervous system such as by trauma, stroke, neurodegenerative diseases or toxic or infective CNS diseases such as encephalitis or meningitis; cardiovascular disorders such as thrombosis; gastrointestinal disorders such as dysfunction of gastrointestinal motility, diabetes insipidus, type II diabetes; and sleep apnea.

A further aspect of the invention is a compound according to formula I for use as therapeutically active substance.

According to another aspect of the present invention, there is provided the use of a compound of formula (I) in the manufacture of a medicament comprising a compound according to formula I for the treatment of disorders of the central nervous system, damage to the central nervous system, cardiovascular disorders, gastrointestinal disorders, diabetes insipidus, type II diabetes, or sleep apnoea.

According to a preferred aspect of this invention the disorders of the central nervous system are selected from depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, obesity, bulimia, anorexia nervosa and premenstrual tension.

According to a preferred aspect of this invention the damage to the central nervous system is by trauma, stroke, neurodegenerative diseases or toxic or infective CNS diseases, particularly wherein the toxic or infective CNS disease is encephalitis or meningitis.

A further preferred embodiment of the present invention is the above-mentioned use, wherein the cardiovascular disorder is thrombosis.

Also preferred is the mentioned use of the compounds according to formula I, wherein the gastrointestinal disorder is dysfunction of gastrointestinal motility.

Particularly preferred is the use of a compound of formula I in the manufacture of a medicament comprising a compound of formula I for the treatment of obesity.

Further preferred is a method of treatment of any of the above mentioned disorders comprising administering to a patient in need of such treatment an effective dose of a compound of formula (I). Also preferred is the use or method as mentioned before, wherein said treatment is prophylactic treatment.

According to a further aspect of the invention there is provided a pharmaceutical composition comprising a compound of formula (I) in combination with a pharmaceutically acceptable carrier or excipient and a method of making such a composition comprising combining a compound of formula (I) with a pharmaceutically acceptable carrier or excipient.

According to a further aspect of the invention there is provided a method of treatment of obesity in a human in need of such treatment which comprises administration to the human a therapeutically effective amount of a compound according to formula I and a therapeutically effective amount of a lipase inhibitor, particularly preferred, wherein the lipase inhibitor is orlistat. Also subject of the present invention is the mentioned method, wherein the administration is simultaneous, separate or sequential.

A further preferred embodiment of the present invention is the use of a compound of the formula I in the manufacture of a medicament for the treatment and prevention of obesity in a patient who is also receiving treatment with a lipase inhibitor, particularly preferred, wherein the lipase inhibitor is orlistat.

Also preferred is the use of a compound in accordance with formula I for the production of medicaments for the treatment and prophylaxis of diabetes mellitus (DM) including Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), diabetes insipidus, hyperglycaemia, diabetic complications and insulin resistance.

Particularly preferred is the use of a compound in accordance with formula I for the production of medicaments for the treatment and prophylaxis of diabetes mellitus (DM) including Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), hyperglycaemia, diabetic complications and insulin resistance.

It is a further particularly preferred object of the invention to provide a compound in accordance with formula I for use in the production of medicaments for the treatment and prophylaxis of Type II diabetes (non-insulin dependent diabetes mellitus (NIDDM)).

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragées and hard gelatin capsules are lactose, other sugars and sugar alcohols like sorbitol, mannitol, maltodextrin, or other fillers; surfactants like sodium lauryl sulfate, Brij 96, or Tween 80; disintegrants like sodium starch glycolate, maize starch or derivatives thereof, polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

The compositions of the present invention maybe formulated in a conventional manner using one or more pharmaceutically acceptable carriers. Thus, the active compounds of the invention may be formulated for oral, buccal, intranasal, parenteral (e.g., intravenous, intramuscular or subcutaneous) transdermal or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropylmethylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (eg. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention maybe formulated for parenteral administration by injection, including using conventional catheterization techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulating agents such as suspending, stabilizing and/or dispersing agents.

Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insulator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., obesity) is 0.1 to 500 mg of the active ingredient per unit dose which could be administered, for example, 1 to 4 times per day.

Assay Procedures

1. Binding to Serotonin Receptors

The binding of compounds of formula (I) to serotonin receptors was determined in vitro by standard methods. The preparations were investigated in accordance with the assays given hereinafter.

Method (a): For the binding to the 5-HT$_{2C}$ receptor the 5-HT$_{2C}$ receptors were radiolabeled with [$^3$H]-5-HT. The affinity of the compounds for 5-HT$_{2C}$ receptors in a CHO cell line was determined according to the procedure of D. Hoyer, G. Engel and H. O. Kalkman, *European J. Pharmacol.*, 1985, 118, 13–23.

Method (b): For the binding to the 5-HT$_{2B}$ receptor the 5-HT$_{2B}$ receptors were radiolabeled with [$^3$H]-5-HT. The affinity of the compounds for human 5-HT$_{2B}$ receptors in a CHO cell line was determined according to the procedure of K. Schmuck, C. Ullmer, P. Engels and H. Lubbert, *FEBS Lett.*, 1994, 342, 85–90.

Method (c): For the binding to the 5-HT$_{2A}$ receptor the 5-HT$_{2A}$ receptors were radiolabeled with [$^{125}$I]-DOI. The affinity of the compounds for 5-HT$_{2A}$ receptors in a CHO cell line was determined according to the procedure of D. J. McKenna and S. J. Peroutka, *J. Neurosci.*, 1989, 9, 3482–90.

The thus determined activity of the compound of the Example is shown in Table 1.

TABLE 1

| Compound | Method (a) Ki (2C) | Method (b) Ki (2B) | Method (c) Ki (2A) |
|---|---|---|---|
| Example 1 | 5.0 nM | 86 nM | 205 nM |
| Example 20 | 2.8 nM | 44 nM | 23 nM |

Preferred compounds of formula I as described above have Ki (2C) values below 10000 nM; especially preferred compounds have Ki (2C) values below 1000 nM, particularly preferred compounds have Ki (2C) values below 100 nM. Most preferred compounds have Ki (2C) values below 30 nM.

2. Functional Activity

The functional activity of compounds of formula (I) was assayed using a Fluorimetric Imaging Plate reader (FLIPR). CHO cells expressing the human 5-HT$_{2C}$ or human 5-HT$_{2A}$ receptors were counted and plated into standard 96 well microtitre plates on the day before testing to give a confluent monolayer. The cells were then dye loaded with the calcium sensitive dye, Fluo-3-AM. Unincorporated dye was removed using an automated cell washer to leave a total volume of 100 µL/well of assay buffer (Hanks balanced salt solution containing 20 mM Hepes and 2.5 mM probenecid). The drug (dissolved in 50 µL of the assay buffer) was added at a rate of 70 µL/sec to each well of the FLIPR 96 well plate during fluorescence measurements. The measurements were taken at 1 sec intervals and the maximum fluorescent signal was measured (approx. 10–15 secs after drug addition) and compared with the response produced by 10 µM 5-HT (defined as 100%) to which it was expressed as a percentage response (relative efficacy). Dose response curves were constructed using Graphpad Prism (Graph Software Inc.).

TABLE 2

| Compound | h5-HT$_{2C}$ EC$_{50}$ Relative (nM) Efficacy (%) | h5-HT$_{2A}$ EC$_{50}$ Relative (nM) Efficacy (%) |
|---|---|---|
| Example 1 | 22 nM (83%) | 640 nM (23%) |
| Example 20 | 7 nM (91%) | 163 nM (49%) |
| Example 21 | 5 nM (80%) | 121 nM (76%) |
| Example 14 | 0.4 nM (88%) | 536 nM (34%) |

The compounds of formula (I) have activity at the h5-HT$_{2C}$ receptor in the range of 10,000 to 0.1 nM.

Preferred compounds of formula I as described above have activity at the h5-HT$_{2C}$ receptor below 1000 nM; especially preferred compounds below 1000 nM, particularly preferred compounds below 100 nM. Most preferred compounds have activity at the h5-HT$_{2C}$ receptor below 30 nM.

EXAMPLES

Example 1 a) (R)-6-Ethyl-4-methyl-1,2,3,4-tetrahydro-pyrazino[1,2-a]indole

Lithium aluminium hydride (532 mg) was added in portions to a solution of (R)-6-ethyl-4-methyl-3,4-dihydro-2H-pyrazino[1,2-a]indol-1-one (800 mg, 3.50 mmol) in tetrahydrofuran (30 mL) and the resulting suspension was heated to reflux for 1 h. After cooling the reaction was quenched by careful addition of 1 M aqueous sodium potassium tartrate solution (50 mL). Then methanol (50 mL) and ethyl acetate (50 mL) were added, the organic layer was separated, washed with brine, dried (MgSO$_4$), and evaporated to yield the title compound (750 mg, 100%). White solid. ISP-MS: m/e=215.3 ([M+H]t).

Intermediates b) (R)-6-Ethyl-4-methyl-3,4-dihydro-2H-pyrazino[1,2-a)indol-1-one.

Potassium tert-butylate (2.17 g, 19.3 mmol) was added to a solution of 7-ethyl-1H-indole-2-carboxylic acid ethyl ester (4.00 g, 18.4 mmol) in N,N-dimethylformamide (100 mL) at 0° C., then after 1 h (S)-5-methyl-2,2-dioxo-[1,2,3]oxathiazolidine-3-carboxylic acid tert-butyl ester (4.81 g, 20.2 mmol) was added and the solution was allowed to reach room temperature over 16 h. The solution was partitioned between 1 M aq. HCl solution (100 mL) and hexane/ethyl acetate 1:1 (200 mL). The organic layer was washed with sat. aq. NaHCO$_3$ solution and brine, dried (MgSO$_4$), and evaporated. The residue was dissolved in dichloromethane (80 mL) and treated with trifluoroacetic acid (20 mL) at 0° C. After removal of the ice bath, the solution was stirred for 30 min, then evaporated under reduced pressure. The residue was dissolved in methanol (100 mL), then after addition of K$_2$CO$_3$ (25.4 g, 184 mmol) the mixture was stirred for 16 h at room temperature. Then water (200 mL) and ethyl acetate (200 mL) were added, the organic layer was separated, washed with brine, dried (MgSO$_4$), and evaporated. Chromatography (70 g SiO$_2$, hexane/ethyl acetate gradient) yielded a foam which was precipitated with hexane to produce the title compound (1.20 g, 29%). White solid. EI-MS: m/e=228.3 (M$^+$). The optical purity was determined by gas chromatography, using a chiral BGB-176-SE column (15 m×0.25 mm), to be 96.2% e.e.

c) 7-Ethyl-indole-1-carboxylic acid tert-butyl ester

7-Ethylindole (106.0 g, 0.73 mol) was dissolved in acetonitrile (1 l) and di-tert-butyl dicarbonate (191.0 g, 0.87 mol) and 4-(dimethylamino)pyridine (4.43 g, 36.0 mmol) were added successively. After 4.5 h the reaction mixture was concentrated and the residue was purified by column chromatography over silica gel (0.032–0.060 mm) with n-hexane/tert-butyl methyl ether (9/1) as eluant to yield the desired product as colorless oil (179 g, 100%). EI-MS: m/e=245.2 ([M]).

d) 7-Ethyl-indole-1,2-dicarboxylic acid 1-tert-butyl ester 2-ethyl ester 2,2,6,6-Tetramethylpiperidine (2.21 g, 15.6 mmol) was dissolved in 30 mL tetrahydrofuran and cooled down to –75° C. n-Butyllithium (9 mL, 14.3 mmol, 1.6M solution in n-hexane) was added while maintaining the temperature below –70° C. After 50 min., a solution of 3.2 g (13.0 mmol) 7-ethyl-indole-1-carboxylic acid tert-butyl ester in 15 mL tetrahydrofuran was added and the temperature again kept below –70° C. After 50 min., ethyl chloroformate (1.4 mL (14.3 mmol) was added and the temperature was allowed to rise to –50° C. After 1 h the reaction mixture was poured into 30 mL saturated aq. ammonium chloride solution and the phases separated. The aqueous phase was extracted once with 50 mL diethyl ether and the combined organic extractions were washed successively with saturated aq. ammonium chloride solution and water, dried over magnesium sulfate, filtered and evaporated. The crude reaction product was flash-chromatographed over silica gel (0.030–0.060 mm) with n-hexane/tert-butyl methyl ether (39/1) as eluant to give the product as a yellow oil (2.3 g, 56.2%). EI-MS: m/e 317.2 ([M]).

e) 7-Ethyl-1H-indole-2-carboxylic acid ethyl ester

7-Ethyl-indole-1,2-dicarboxylic acid 1-tert-butyl ester 2-ethyl ester (76.6 g, 0.24 mol) was dissolved in 450 mL dichloromethane and cooled to 0° C. Trifluoroacetic acid (150.0 mL, 1.96 mol) was added within 30 min. and after an additional 45 min. the reaction mixture was concentrated at a rotary evaporator. The residue was dissolved in 300 mL dichloromethane and poured cautiously onto 500 mL saturated aq. sodium bicarbonate solution. The phases were separated and the aqueous phase was extracted twice with dichloromethane. The combined organic extracts were washed with brine, dried over magnesium sulfate, filtered and concentrated on a rotary evaporator. The residue was suspended in 400 mL n-hexane and put in an ultrasonic bath for 15 min. The suspension was filtered and the filter cake was washed with 100 mL n-hexane. This procedure was repeated to give the desired product as a light brown solid (40.2 g, 76.6%). EI-MS: m/e 217.1 ([M]).

f) (S)-5-Methyl-2,2-dioxo-[1,2,3]oxathiazolidine-3-carboxylic acid tert-butyl ester To a solution of 11.15 g (S)-Carbamic acid, (2-hydroxypropyl)-, 1,1-dimethylethyl ester, in 100 mL tetrahydrofuran was added at –78° C. 80 mL of a 1.6 M solution of n-butyllithium in n-hexane during 15 min. The resulting mixture was warmed to –15° C. and stirred for 45 min. A solution of 7.5 g thionyl chloride in 50 mL tetrahydrofuran was added during 5 min. The mixture was then warmed to –15° C. and stirred for 90 min. The reaction mixture was partitioned between ethyl acetate and 10% citric acid. The phases were separated and the organic phase was washed with sodium bicarbonate and brine, dried over magnesium sulfate, evaporated and purified by chromatography on silica gel with 3:1 hexane:ethyl acetate. The intermediate sulfamidite was taken up in 60 mL ethyl acetate and 100 mL of a 10% solution of sodium metaperiodate was added. The mixture was cooled to 0° C. and 0.21 g ruthenium dioxide dihydrate was added and the mixture was stirred at this temperature for 45 min. The phases were separated and the organic phase was purified by chromatography on silica gel with 2:1 hexane:ethyl acetate to yield 5.3 g of the title compound as white crystals after recrystallisation from ethanol (m.p.: 111.6–115° C.) $\alpha_D^{20}$=+37.1.

Example 2 a) (R)-4-Methyl-7-trifluoromethyl-1,2,3,4-tetrahydro-pyrazino[1,2-a]indole

The title compound, ISP-MS: m/e=255.1 ([M+H]$^+$), was produced in accordance with the general method of example 1a) fr®(R)-4-methyl-7-trifluoromethyl-3,4-dihydro-2H-pyrazino[1,2-a]indol-1-one. Yellow solid, m.p. 123–125° C.

Intermediate b) (R)-4-Methyl-7-trifluoromethyl-3,4-dihydro-2H-pyrazino[1,2-a]indol-1-one.

The title compound (EI-MS: m/e=268.2 (M$^+$)) was produced in accordance with the general method of example 1b) from 6-trifluoromethyl-1H-indole-2-carboxylic acid ethyl ester and (S)-5-methyl-2,2-dioxo-[1,2,3]oxathiazolidine-3-carboxylic acid tert-butyl ester. White solid, m.p. 201–204° C.

Example 3 a) (R)-7-Bromo-4-methyl-1,2,3,4-tetrahydro-pyrazino[1,2-a]indole

The title compound, ISP-MS: m/e=265.2, 267.2 ([M+H]$^+$), was produced in accordance with the general method of example 1a) fr®(R)-7-bromo-4-methyl-3,4-dihydro-2H-pyrazino[1,2-a]indol-1-one. Colorless amorphous solid.

Intermediate b) (R)-7-Bromo-4-methyl-3,4-dihydro-2H-pyrazino[1,2-a]indol-1-one.

The tide compound (EI-MS: m/e=279.1, 281.1 (M$^+$)) was produced in accordance with the general method of example 1b) from 6-bromo-1H-indole-2-carboxylic acid ethyl ester and (S)-5-methyl-2,2-dioxo-[1,2,3]oxathiazolidine-3-carboxylic acid tert-butyl ester. Colorless amorphous solid.

Example 4 a) (R)-9-Chloro-4-methyl-1,2,3,4-tetrahydro-pyrazino[1,2-a]indole hydrochloride

The tide compound, ISP-MS: m/e=221.2 ([M+H–Cl]$^+$), was produced in accordance with the general method of example 1a) from (R)-9-chloro-4-methyl-3,4-dihydro-2H-pyrazino[1,2-a]indol-1-one and crystallised as HCl salt. Colorless solid, m.p. 234–237° C. dec.

Intermediate b) (R)-9-Chloro-4-methyl-3,4-dihydro-2H-pyrazino[1,2-a]indol-1-one.

The title compound (EI-MS: m/e=234.1 (M$^+$)) was produced in accordance with the general method of example 1b) from 4-chloro-1H-indole-2-carboxylic acid ethyl ester and (S)-5-methyl-2,2-dioxo-[1,2,3]oxathiazolidine-3-carboxylic acid tert-butyl ester. Colorless solid, m.p. 180–184¢C.

Example 5 a) (R)-7-Chloro-8-fluoro-4-methyl-1,2,3,4-tetrahydro-pyrazino[1,2-a]indole.

The title compound, ISP-MS: m/e=239.2 ([M+H]$^+$), was produced in accordance with the general method of example 1a) from (R)-7-chloro-8-fluoro-4-methyl-3,4-dihydro-2H-pyrazino[1,2-a]indol-1-one. Colorless amorphous solid.

Intermediate b) (R)-7-Chloro-8-fluoro-4-methyl-3,4-dihydro-2H-pyrazino[1,2-a]indol-1-one.

The title compound (EI-MS: m/e=253.1 (M$^+$)) was produced in accordance with the general method of example 1b) from 6-chloro-5-fluoro-1H-indole-2-carboxylic acid ethyl ester and (S)-5-methyl-2,2-dioxo-[1,2,3]oxathiazolidine-3-carboxylic acid tert-butyl ester. Colorless solid, m.p. >250° C.

Example 6 a) (R)-4,8-Dimethyl-7-trifluoromethyl-1,2,3,4-tetrahydro-pyrazino[1,2-a]indole hydrochloride The title compound, ISP-MS: m/e=269.3 ([M+H]$^+$), was produced in accordance with the general method of example 1a) from (R)-4,8-dimethyl-7-trifluoromethyl-3,4-dihydro-2H-pyrazino[1,2-a]indol-1-one.

Intermediates b) (R)-4,8-Dimethyl-7-trifluoromethyl-3,4-dihydro-2H-pyrazino[1,2-a)indol-1-one The title compound (EI-MS: m/e=253.1 (M$^+$)) was produced in accordance with the general method of example 1b) from 5-methyl-6-trifluoromethyl-1H-indole-2-carboxylic acid ethyl ester and (S)-5-methyl-2,2-dioxo-[1,2,3]oxathiazolidine-3-carboxylic acid tert-butyl ester. Colorless solid, m.p. >250° C.

c) 5-Methyl-6-trifluoromethyl-1H-indole-2-carboxylic acid ethyl ester

The title compound (EI-MS: m/e=271.1 (M$^+$)) was produced in accordance with the general method of example 1c to 1e) from 5-methyl-6-trifluoromethyl-1H-indole. Colorless solid, m.p. 176–178° C.

Example 7 a) (R)-7,9-Dichloro-4-methyl-1,2,3,4-tetrahydro-pyrazino[1,2-a]indole hydrochloride The title compound (ISP-MS: m/e=255.1 ([M+H$^+$])) was produced in accordance with the general method of example 1a) from (R)-7,9-dichloro-4-methyl-3,4-dihydro-2H-pyrazino[1,2-a]indol-1-one and was crystallised as the HCl salt. Colorless amorphous solid.

Intermediate b) (R)-7,9-Dichloro-4-methyl-3,4-dihydro-2H-pyrazino[1,2-a]indol-1-one 101411 The title compound (ISP-MS: m/e=269.2 ([M+H$^+$])) was produced in accordance with the general method of example 1b) from 4,6-dichloro-1H-indole-2-carboxylic acid ethyl ester and (S)-5-methyl-2,2-dioxo-[1,2,3]oxathiazolidine-3-carboxylic acid tert-butyl ester. Colorless solid.

Example 8 a) (R)-6,9-Difluoro-4-methyl-1,2,3,4-tetrahydro-pyrazino[1,2-a]indole hydrochloride The title compound (ISP-MS: m/e=223.2 ([M+H$^+$])) was produced in accordance with the general method of example 1a) from (R)-6,9-difluoro-4-methyl-3,4-dihydro-2H-pyrazino[1,2-a]indol-1-one and was crystallised as HCl salt. Colorless amorphous solid.

Intermediate b) (R)-6,9-Difluoro-4-methyl-3,4-dihydro-2H-pyrazino[1,2-a]indol-1-one The title compound (ISP-MS: m/e=237.1 ([M+H$^+$])) was produced in accordance with the general method of example 1b) from 4,7-difluoro-1H-indole-2-carboxylic acid ethyl ester and (S)-5-methyl-2,2-dioxo-[1,2,3]oxathiazolidine-3-carboxylic acid tert-butyl ester. Colorless solid.

Example 9 a) (R)-6-Fluoro-4-methyl-1,2,3,4-tetrahydro-pyrazino[1,2-a]indole

The title compound (ISP-MS: m/e 205.2 ([M+H$^+$])) was produced in accordance with the general method of example 1a) from (R)-6-fluoro-4-methyl-3,4-dihydro-2H-pyrazino[1,2-a]indol-1-one. Yellow oil.

Intermediate b) (R)-6-Fluoro-4-methyl-3,4-dihydro-2H-pyrazino[1,2-a]indol-1-one

The title compound (ISP-MS: m/e=219.2 ([M+H$^+$])) was produced in accordance with the general method of example 1b) from 7-fluoro-1H-indole-2-carboxylic acid ethyl ester and (S)-5-methyl-2,2-dioxo-{[1,2,3]oxathiazolidine-3-carboxylic acid tert-butyl ester. Colorless solid.

Example 10 a) (R)-4,6-Dimethyl-1,2,3,4-tetrahydro-pyrazino[1,2-a]indole

The title compound (ISP-MS: m/e=201.2 ([M+H$^+$])) was produced in accordance with the general method of example 1a) from (R)-4,6-dimethyl-3,4-dihydro-2H-pyrazino[1,2-a]indol-1-one. Yellow oil.

Intermediate b) (R)-4,6-Dimethyl-3,4-dihydro-2H-pyrazino[1,2-a]indol-1-one

The title compound (ISP-MS: m/e=215.3 ([M+H$^+$])) was produced in accordance with the general method of example 1b) from 7-methyl-1H-indole-2-carboxylic acid ethyl ester and (S)-5-methyl-2,2-dioxo-[1,2,3]oxathiazolidine-3-carboxylic acid tert-butyl ester. Colorless oil.

Example 11 a) (R)-8-Fluoro-4-methyl-1,2,3,4-tetrahydro-pyrazino[1,2-a]indole

The title compound (ISP-MS: m/e 205.2 ([M+H$^+$])) was produced in accordance with the general method of example 1a) from (R)-8-fluoro-4-methyl-3,4-dihydro-2H-pyrazino[1,2-a]indol-1-one. Yellow oil.

Intermediate b) (R)-8-Fluoro-4-methyl-3,4-dihydro-2H-pyrazino[1,2-a]indol-1-one

The title compound (ISP-MS: m/e=219.2 ([M+H$^+$])) was produced in accordance with the general method of example 1b) from 5-fluoro-1H-indole-2-carboxylic acid ethyl ester and (S)-5-methyl-2,2-dioxo-[1,2,3]oxathiazolidine-3-carboxylic acid tert-butyl ester. Colorless solid.

Example 12 a) (R)-7-Bromo-9-fluoro-4-methyl-1,2,3,4-tetrahydro-pyrazino[1,2-a]indole

The title compound (ISP-MS: m/e=285.0 ([M+H$^+$])) was produced in accordance with the general method of example 1a) from (R)-7-bromo-9-fluoro-4-methyl-3,4-dihydro-2H-pyrazino[1,2-a]indol-1-one. Colorless solid.

Intermediate b) (R)-7-Bromo-9-fluoro-4-methyl-3,4-dihydro-2H-pyrazino[1,2-a]indol-1-one The title compound (ISP-MS: r/e=297.2 ([M+H$^+$])) was produced in accordance with the general method of example 1b) from 6-bromo-4-fluoro-1H-indole-2-carboxylic acid ethyl ester and (S)-5-methyl-2,2-dioxo-[1,2,3]oxathiazolidine-3-carboxylic acid tert-butyl ester. Colorless solid.

Example 13 a) (R)-7-Chloro-10-methoxy-4-methyl-1,2,3,4-tetrahydro-pyrazino[1,2-a]indole

The title compound, ISP-MS: m/e=251.2 ([M+H]I), was produced in accordance with the general method of example 1a) from (R)-7-chloro-10-methoxy-4-methyl-3,4-dihydro-2H-pyrazino[1,2-a]indol-1-one. Yellow oil.

Intermediate b) (R)-7-Chloro-10-methoxy-4-methyl-3,4-dihydro-2H-pyrazino[1,2-a]indol-1-one The title compound (EI-MS: m/e=264.1 (M$^+$)) was produced in accordance with the general method of example 1b) from 6-chloro-3-methoxy-1H-indole-2-carboxylic acid ethyl ester and (S)-5-methyl-2,2-dioxo-[1,2,3]oxathiazolidine-3-carboxylic acid tert-butyl ester. White solid.

Example 14 a) (R)-7-Chloro-4,6,10-trimethyl-1,2,3,4-tetrahydro-pyrazino[1,2-a]indole oxalate Lithium aluminium hydride (64 mg, 1.67 mmol) was added in portions to a solution of (R)-7-chloro-4,6,10-trimethyl-3,4-dihydro-2H-pyrazino[1,2-a]indol-1-one (200 mg, 0.76 mmol) and the resulting suspension was heated to reflux for 5 h. After cooling the reaction was quenched by careful addition of 1 M aqueous sodium potassium tartrate solution (20 mL). Then ether (20 mL) was added; the organic layer was separated, washed with brine, dried (Na$_2$SO$_4$), and evaporated. The residue was dissolved in ether (3 mL) and treated with a solution of oxalic acid (200 mg, 2.22 mmol) in ethanol (1 mL). The precipitate was collected by filtration and dried to yield the title compound (116 mg, 45%). Off-white solid. ISP-MS: m/e=249.2 ([M+H-C$_2$H$_2$O$_4$]+). Anal. calc. for C$_{16}$H$_{19}$ClN$_2$O$_4$ (338.79): C 56.72; H 5.65; N 8.27; found: C 56.64; H 5.41; N 8.22.

Intermediate b) (R)-7-Chloro-4,6,10-trimethyl-3,4-dihydro-2H-pyrazino[1,2-a]indol-1-one The title compound (EI-MS: m/e=262.1 (M$^+$)) was produced in accordance with the general method of example 1b) from 6-chloro-3,7-dimethyl-1H-indole-2-carboxylic acid ethyl ester and (S)-5-methyl-2,2-dioxo-[1,2,3]oxathiazolidine-3-carboxylic acid tert-butyl ester. White solid.

Example 15 a) (RS)-7-Bromo-4-ethyl-1,2,3,4-tetrahydro-pyrazino[1,2-a]indole

The title compound, ISP-MS: m/e=279.1, 281.2 ([M+H]I), was produced in accordance with the general method of example 1a) from (RS)-7-bromo-4-ethyl-3,4-dihydro-2H-pyrazino[1,2-a]indol-1-one. Colorless oil. The enantiomeres can be separated by methods known in the art such as chromatography. It can be obtained (S)-7-bromo-4-ethyl-1,2,3,4-tetrahydro-pyrazino[1,2-a]indole. Further it can be obtained the preferred (R)-7-bromo-4-ethyl-1,2,3,4-tetrahydro-pyrazino[1,2-a]indole.

Intermediate b) (RS)-7-Bromo-4-ethyl-3,4-dihydro-2H-pyrazino[1,2-a]indol-1-one

The title compound (ISP-MS: m/e=293.2, 295.2 (M+H]$^+$)) was produced in accordance with the general method of example 1b) from 6-bromo-1H-indole-2-carboxylic acid ethyl ester and (RS)-5-ethyl-2,2-dioxo-[1,2,3]oxathiazolidine-3-carboxylic acid tert-butyl ester. White solid.

Example 16 a) (R)-7-Bromo-4-ethyl-1,2,3,4-tetrahydro-pyrazino[1,2-a]indole.

(RS)-7-Bromo-4-ethyl-1,2,3,4-tetrahydro-pyrazino[1,2-a]indole (230 mg, 0.82 mmol) was subjected to chromatographic separation using a Chiralcel® OD-H column and heptane/2-propanol 95:5 as the eluant. This yielded the title compound (89 mg, 39%; colorless oil; EI-MS: m/e=278.1 (M$^+$); $\alpha_D^{20}$: -65.8° (c=0.25, CH$_2$Cl$_2$), and its enantiomer (S)-7-bromo-4-ethyl-1,2,3,4-tetrahydro-pyrazino[1,2-a]indole (89 mg, 39%). Colorless oil. $\alpha_D^{20}$: +65.0° (c=0.32, CH$_2$Cl$_2$).

Example 17 a) (R)-4-Methyl-6-trifluoromethoxy-1,2,3,4-tetrahydro-pyrazino[1,2-a]indole

A solution of (R)-4-methyl-6-trifluoromethoxy-3,4-dihydro-2H-pyrazino[1,2-a]indol-1-one (800 mg, 2.81 mmol) in tetrahydrofuran (4 ml.) was added to a suspension of lithium aluminium hydride (420 mg, 11.1 mmol) in tetrahydrofuran (4 mL) and the resulting mixture was heated to reflux for 90 min. After cooling the reaction mixture was slowly added to a cooled saturated aqueous sodium potassium tartrate solution. The resulting suspension was filtered on dicalite and the organics extracted twice with ethyl acetate. The combined organic phases were washed with brine, dried (Na$_2$SO$_4$), and evaporated. The residue was purified by column chromatography on silica gel (n-hexane/ethyl acetate to ethyl acetate/methanol gradient) to yield the title compound as a light yellow solid (385 mg, 51%). Mp: 58–60° C.; EI-MS: m/e=270.1 (M$^+$).

Intermediates b) (R)-4-Methyl-6-trifluoromethoxy-3,4-dihydro-2H-pyrazino[1,2-a]indol-1-one.

Sodium hydride (280 mg of a 60% dispersion in mineral oil, 7 mmol) was added to a solution of 7-trifluoromethoxy-1H-indole-2-carboxylic acid ethyl ester (1.53 g, 5.6 mmol) and (S)-5-methyl-2,2-dioxo-[1,2,3]oxathiazolidine-3-carboxylic acid tert-butyl ester (1.53 g, 6.45 mmol) in N,N-dimethylformamide (15 mL) at 0° C. The solution was allowed to reach room temperature and stirred 36 h. Further amounts of sodium hydride (56 mg) and (S)-5-methyl-2,2-dioxo-[1,2,3]oxathiazolidine-3-carboxylic acid tert-butyl ester (306 mg) were added to complete the reaction. To the solution was added 10% aq. citric acid solution and the mixture stirred 1 h at room temperature. The organics were extracted with ethyl acetate (2×), the combined organic phases washed with sat. aq. NaHCO$_3$ solution and brine, dried (Na$_2$SO$_4$), and evaporated. The residue was dissolved in dichloromethane (25 mL), cooled to 0° C. and treated with trifluoroacetic acid (12 mL). After removal of the ice bath, the solution was stirred for 30 min and evaporated under reduced pressure. The residue was taken up in methanol (20 mL) and K$_2$CO$_3$ (2.52 g, 19.5 mmol) added, and the mixture stirred 15 h at room temperature. The mixture was filtered, the filtrate diluted with ethyl acetate, washed with water, dried ($Na_2SO_4$) and evaporated. The residue was purified by column chromatography on silica gel (hexane/ethyl acetate gradient) to afford the product as a pale yellow foam (89 mg, 64%). ISP-MS: m/e=285.1 ($M^+$+H).

c) 7-Trifluoromethoxy-1H-indole-2-carboxylic acid ethyl ester

The title compound (EI-MS: m/e 273.1 ($M^+$)) was produced in accordance with the general method of example 1c to 1e) from 7-trifluoromethoxy-1H-indole. Light brown amorphous solid.

d) 7-Trifluoromethoxy-1H-indole

Potassium hydroxide (17.9 g, 321 mmol) was boiled for 2 h in t-butanol (500 mL). (2-Trifluoromethoxy-6-trimethylsilanylethynyl-phenyl)-carbamic acid ethyl ester (52.8 g, 153 mmol) dissolved in t-butanol (500 mL) was added and boiling was continued for 2 h. The solvent was removed in vacuo and the residue was partitioned between diethyl ether and water. The organic phases were washed with brine, pooled and dried with $MgSO_4$. Evaporation of the solvent yielded 31.8 g of brownish oil, which was purified by chromatography on silica gel with hexane/ethylacetate (9:1). This yielded the title compound, (30.2 g, 98%) as a yellow oil. (EI-MS: m/e=201.0 ($M^+$)).

e) (2-Trifluoromethoxy-6-trimethylsilanylethynyl-phenyl)-carbamic acid ethyl ester Bis(triphenylphosphine)palladium(II) dichloride (1.1 g, 1.6 mmol) and copper(I) iodide (0.3 g, 1.6 mmol) were added to triethylamine (600 mL) and heated with stirring for 20 min. The mixture was cooled to room temperature and (2-iodo-6-trifluoromethoxy-phenyl)-carbamic acid ethyl ester (60.2 g, 160 mmol) was added. After stirring for 30 min at room temperature trimethylsilylacetylene (21.1 g, 152 mmol) was added and the mixture was stirred for another 2 h at room temperature. Triethylamine was removed in vacuo and the residue was partitioned between water and diethyl ether. The organic phases were washed with 1N HCl, brine, pooled and dried with $MgSO_4$. Evaporation of the solvent yielded 57 g of brownish solid, which was purified by chromatography on silica gel with hexane/ethyl acetate (9:1). This yielded the title compound, (52.8 g, 95%) as a beige amorphous solid. (EI-MS: m/e 345.0 ($M^+$)).

f) (2-Iodo-6-trifluoromethoxy-phenyl)-carbamic acid ethyl ester (2-Trifluoromethoxy-phenyl)-carbamic acid ethyl ester (42.4 g, 0.17 mol) was dissolved in THF (800 mL) and cooled to –70° C. sec-BuLi in cyclohexane (280 mL, 1.3 M) was added dropwise at this temperature with stirring. Stirring was continued for 1 h after addition was complete. A solution of iodine (43.2 g, 0.17 mol) in THF (160 mL) was added dropwise at –70° C. Stirring was continued for 1 h after addition was complete and the mixture was hydrolysed with saturated ammonium chloride solution. Water was added and the mixture was extracted with diethyl ether. The organic phases were washed with 40% sodium bisulfite, water, brine, pooled and dried with $MgSO_4$. Evaporation of the solvent yielded the title compound, (60.2 g, 94%) as a colorless amorphous solid. (EI-MS: m/e=374.9 ($M^+$)).

g) (2-Trifluoromethoxy-phenyl)-carbamic acid ethyl ester 2-(Trifluoromethoxy)aniline (50 g, 0.282 mol) was dissolved in DME (1000 mL) and cooled to –5° C. Sodium hydride (12.3 g, 55%, 0.282 mol) was added in portions and the suspension was allowed to warm to room temperature. Ethyl chloroformate (23.5 mL, 0.245 mol) was added drop by drop and the mixture was stirred for 2 h at room temperature and for 1.5 h at reflux after addition was complete. Hydrolysis was with water (110 mL). The phases were separated and the water phase was extracted with ethyl acetate. The organic phases were washed with brine, pooled and dried with $MgSO_4$. Evaporation of the solvent yielded 70.6 g of brown oil, which was purified by chromatography on silica gel with hexane/ethyl acetate (6:1). This yielded the title compound, (44.2 g, 62%) as a beige yellow oil. (EI-MS: m/e=249.1 ($M^+$)).

Example 18 a) (R)-7-Chloro-4-ethyl-1,2,3,4-tetrahydro-pyrazino[1,2-a]indole

The title compound (ISP-MS: m/e=235.3 ([$M+H^+$])) was produced in accordance with the general method of example 1a) from (R)-7-chloro-4-ethyl-3,4-dihydro-2H-pyrazino[1,2-a]indol-1-one. Yellow oil.

Intermediate b) (R)-7-Chloro-4-ethyl-3,4-dihydro-2H-pyrazino[1,2-a]indol-1-one

The title compound (ISP-MS: m/e=249.2 ([$M+H^+$])) was produced in accordance with the general method of example 1b) from 6-chloro-1H-indole-2-carboxylic acid ethyl ester and (RS)-5-ethyl-2,2-dioxo-[1,2,3]oxathiazolidine-3-carboxylic acid tert-butyl ester followed by a chromatographic separation of the enantiomers on a ChiralPak AD-column according to example 16a. Light brown solid.

Example 19 a) (R)-4-Methyl-7,9-bis-trifluoromethyl-1,2,3,4-tetrahydro-pyrazino[1,2-a]indole The title compound (ISP-MS: m/e=322.1 ([M+])) was produced in accordance with the general method of example 1a) from (R)-4-methyl-7,9-bis-trifluoromethyl-3,4-dihydro-2H-pyrazino 1,2-a]indol-1-one. Yellow oil.

Intermediate b) (R)-4-Methyl-7,9-bis-trifluoromethyl-3,4-dihydro-2H-pyrazino[1,2-a]indol-1-one The title compound (ISP-MS: m/e=336.0([M+])) was produced in accordance with the general method of example 1b) from 4,6-bis-trifluoromethyl-1H-indole-2-carboxylic acid ethyl ester and (S)-5-methyl-2,2-dioxo-[1,2,3]oxathiazolidine-3-carboxylic acid tert-butyl ester.

Example 20 a) (R)-7-Chloro-4-methyl-1,2,3,4-tetrahydro-pyrazino[1,2-a]indole

The title compound (ISP-MS: m/e 221.3 ([$M+H^+$])) was produced in accordance with the general method of example 1a) from (R)-7-chloro-4-methyl-3,4-dihydro-2H-pyrazino [1,2-a]indol-1-one. Yellow solid.

Intermediate b) (R)-7-Chloro-4-methyl-3,4-dihydro-2H-pyrazino[1,2-a]indol-1-one

The title compound (ISP-MS: m/e=235.2 ([$M+H^+$])) was produced in accordance with the general method of example 1b) from 6-chloro-1H-indole-2-carboxylic acid ethyl ester and (S)-5-methyl-2,2-dioxo-[1,2,3]oxathiazolidine-3-carboxylic acid tert-butyl ester. Off-white solid.

Example 21 a) (R)-4,6,9-Trimethyl-1,2,3,4-tetrahydro-pyrazino[1,2-a]indole

The title compound (ISP-MS: m/e=215.4 ([$M+H^+$])) was produced in accordance with the general method of example 1a) from (R)-4,6,9-trimethyl-3,4-dihydro-2H-pyrazino[1,2-a]indol-1-one. Yellow oil.

Intermediate b) (R)-4,6,9-Trimethyl-3,4-dihydro-2H-pyrazino[1,2-a]indol-1-one

The title compound (ISP-MS: m/e=229.2 ([M+H⁺])) was produced in accordance with the general method of example 1b) from 4,7-dimethyl-1H-indole-2-carboxylic acid ethyl ester and (S)-5-methyl-2,2-dioxo-[1,2,3]oxathiazolidine-3-carboxylic acid tert-butyl ester. Yellow foam.

Example 22 a) (R)-4,6,7-Trimethyl-1,2,3,4-tetrahydro-pyrazino[1,2-a]indole

The tide compound (ISP-MS: m/e=215.4 ([M+H+1])) was produced in accordance with the general method of example 1a) from (R)-4,6,7-trimethyl-3,4-dihydro-2H-pyrazino[1,2-a]indol-1-one. Yellow solid.

Intermediate b) (R)-4,6,7-Trimethyl-3,4-dihydro-2H-pyrazino[1,2-a]indol-1-one

The title compound (ISP-MS: m/e=229.2 ([M+H⁺])) was produced in accordance with the general method of example 1b) from 6,7-dimethyl-1H-indole-2-carboxylic acid ethyl ester and (S)-5-methyl-2,2-dioxo-[1,2,3]oxathiazolidine-3-carboxylic acid tert-butyl ester. Yellow foam.

Example 23 a) (R)-7-Chloro-4,6-dimethyl-1,2,3,4-tetrahydro-pyrazino[1,2-a]indole

The title compound (ISP-MS: m/e=235.2 ([M+H⁺])) was produced in accordance with the general method of example 1a) from (R)-7-chloro-4,6-dimethyl-3,4-dihydro-2H-pyrazino[1,2-a]indol-1-one. Yellow low-melting solid.

Intermediate b) (R)-7-Chloro-4,6-dimethyl-3,4-dihydro-2H-pyrazino[1,2-a]indol-1-one The title compound (ISP-MS: m/e=248.1 ([M⁺])) was produced in accordance with the general method of example 1b) from 6-chloro-7-methyl-1H-indole-2-carboxylic acid ethyl ester and (S)-5-methyl-2,2-dioxo-[1,2,3]oxathiazolidine-carboxylic acid tert-butyl ester. Yellow low-melting solid.

Example 24 a) (R)-4,8-Dimethyl-1,2,3,4-tetrahydro-pyrazino[1,2-a]indole

The title compound (ISP-MS: m/e=200.2 ([M+])) was produced in accordance with the general method of example 1a) from (R)-4,8-dimethyl-3,4-dihydro-2H-pyrazino[1,2-a]-1-one. Waxy solid.

Intermediate b) (R)-4,8-Dimethyl-3,4-dihydro-2H-pyrazino[1,2-a]indol-1-one

The title compound (ISP-MS: m/e=214.2 ([M⁺])) was produced in accordance with the general method of example 1b) from 5-methyl-1H-indole-2-carboxylic acid ethyl ester and (S)-5-methyl-2,2-dioxo-[1,2,3]oxathiazolidine-3-carboxylic acid tert-butyl ester. Waxy solid.

Example 25 a) (R)-8-Fluoro-1-methyl-7-trifluoromethyl-1,2,3,4-tetrahydro-pyrazino[1,2-a]indole The title compound (ISP-MS: m/e=273.2 ([M+H⁺])) was obtained according to example 16a by chiral chromatography on a ChiralPak AD-column of the racemic mixture. Light yellow solid.

Intermediate b) (RS8-Fluoro-1-methyl-7-trifluoromethyl-1,2,3,4-tetrahydro-pyrazino[1,2-a]indole The title compound (ISP-MS: m/e=272.1 ([M+])) was produced from [2-(2-acetyl-5-fluoro-6-trifluoromethyl-indol-1-yl)-ethyl]-carbamic acid tert-butyl ester as follows: [2-(2-Acetyl-5-fluoro-6-trifluoromethyl-indol-1-yl)-ethyl]-carbamic acid tert-butyl ester (205 mg) was dissolved in methylene chloride (6 mL) and was treated at room temperature with trifluoroacetic add (6 mL) for one hour. The reaction mixture was poured into aqueous NaOH and the pH was brought to 14. The mixture was extracted three times with ethyl acetate, the organic phases were pooled, dried over sodium sulfate and the solvent was removed. The residue was taken up in ether (15 mL) and treated with lithium aluminium hydride (50 mg). The reaction was refluxed for three hours. The reaction mixture was poured in aqueous hydrochloric acid. The mixture was extracted three times with ethyl acetate, the organic phases were pooled, dried over sodium sulfate and the solvent was removed. The residue was chromatographed on silica gel (eluant: 95/5 methylene chloride/methanol). The title compound was obtained as a light yellow resin in 78% yield.

c) [2-(2-Acetyl-5-fluoro-6-trifluoromethyl-indol-1-yl)-ethyl]-carbamic acid tert-butyl ester The title compound (ISP-MS: m/e=272.1 ([M+])) was produced from 2-[1-(tert-butyl-dimethyl-silanyloxy)-ethyl]-5-fluoro-6-trifluoromethyl-1H-indole as follows: 2-[1-(tert-Butyl-dimethyl-silanyloxy)-ethyl]-5-fluoro-6-trifluoromethyl-1H-indole (1520 mg) was dissolved in tetrahydrofuran (30 mL) and was treated at 0° C. with sodium hydride (275 mg; 50% in oil), after 30 min, 2,2-dioxo-[1,2,3]oxathiazolidine-3-carboxylic acid tert-butyl ester (1410 mg) was added and the reaction was allowed to proceed overnight. The reaction mixture was poured into aqueous hydrochloric acid. The mixture was extracted three times with ethyl acetate, the organic phases were pooled, dried over sodium sulfate and the solvent was removed. The residue was chromatographed on silica gel (eluant: hexane/ethyl acetate 85/15). 1.47 g N-alkylated product (69% yield) was obtained.

This compound (1.43 g) was dissolved in tetrahydrofuran (20 mL) and was treated with N-tetrabutyl ammonium fluoride (3 equivalents) and stirred 5 h. The reaction mixture was poured into brine. The mixture was extracted three times with ethylacetate, the organic phases were pooled, dried over sodium sulfate and the solvent was removed. The residue was chromatographed on silica gel (eluant: hexane/isopropanol 87/13). 1.04 g of deprotected compound (94% yield) was obtained.

This compound (250 mg) was dissolved in dichloromethane (8 mL) and treated with manganese dioxide (15 equivalents) then stirred 18 h. The reaction mixture was filtered through dicalite and the solvent was removed. The residue was chromatographed on silica-gel (eluant: hexane/ethyl acetate 65/35) to give 214 mg of the title-compound (86% yield) as a light yellow solid.

d) 2-[1-(tert-Butyl-dimethyl-silanyloxy)-ethyl]-5-fluoro-6-trifluoromethyl-1H-indole The title compound (ISP-MS: m/e=361.2 ([M⁺])) was produced from (4-fluoro-2-iodo-5-trifluoromethyl-phenyl)-carbamic acid methyl ester as follows: (4-Fluoro-2-iodo-5-trifluoromethyl-phenyl)-carbamic acid methyl ester (1520 mg) was dissolved in triethylamine (20 mL). Bis-(triphenylphosphine)-palladium (II) dichloride (193 mg; 5 mol %), copper (I) iodide (52 mg; 5 mol %) and tert-butyl-dimethyl-(1-methyl-prop-2-ynyloxy)-silane (1.22 g; 1.2 equivalent) were added and the reaction mixture was heated 3 h at 50° C. under exclusion of oxygen. The reaction mixture was poured into chilled aqueous hydrochloric acid (25%) and extracted three times with ethyl acetate. The organic phases were pooled, dried over sodium sulfate and the solvent was removed. The residue was chromatographed on silica gel (eluant: hexane/ethyl acetate 95/5). 2.44 g of the {2-[3-(tert-butyl-dimethyl-silanyloxy)-but-1-ynyl]-4-fluoro-5-trifluoromethyl-phenyl}-carbamic acid methyl ester (quantitative yield) was obtained.

This compound (2.31 g) was dissolved in tetrahydrofuran (35 mL), treated with 2N aqueous lithium hydroxide (6 equivalents) and heated under refluxfor 4 h. The reaction mixture was poured into brine. The mixture was extracted three times with ethyl acetate, the organic phases were pooled, dried over sodium sulfate and the solvent was removed. The residue was chromatographed on silica-gel (eluant: hexane/ethyl acetate 95/5). The title compound (1.54 g; 77% yield) was obtained as a brown liquid.

Example 26 a) (R)-8-Bromo-4,7-dimethyl-1,2,3,4-tetrahydro-pyrazino [1,2-a]indole hydrochloride A solution of 0.12 g (R)-8-bromo-4,7-dimethyl-1,2,3,4-tetrahydro-pyrazino[1,2-a]indole-2-carboxylic acid tert-butyl ester in 3 mL of a 2M solution of hydrochloric acid in ethyl acetate was stirred at room temperature under argon for 2 h. The precipitate was collected by filtration and dried to constant weight to yield the title compound (0.065 g) as off-white crystals. m.p.: 241° C. (dec.); MS: M+H=279.1; HNMR: (250 MHz, DMSO-d6, δ [ppm]) 1.50 (d, J=6.5 Hz, 3H); 2.45 (s, 3H); 3.48–3.74 (m, 2H); 4.36–4.58 (m, 2H); 4.74–4.89 (m, 1H); 6.35 (s, 1H); 7.54 (s, 1H); 7.78 (s, 1H).

Intermediates b) (R)-8-Bromo-4,7-dimethyl-1,2,3,4-tetrahydro-pyrazino [1,2-a]indole-2-carboxylic acid tert-butyl ester A mixture of 0.75 g (R)-(2-15-bromo-2-[dimethyl-(1,1,2-trimethyl-propyl)-silanyloxymethyl]-6-methyl-indol-1-yl}-propyl)-carbamic acid tert-butyl ester and 0.52 g ammonium fluoride in 7.5 mL methanol was stirred 18 h at room temperature. The reaction mixture was partitioned between water and ethyl acetate. The phases were separated and the organic phase was washed with 10% citric acid, 10% sodium bicarbonate and brine, dried over magnesium sulfate and evaporated to dryness. The residue was taken up in 6 mL dichloromethane and 0.59 g manganese dioxide was added. The mixture was stirred 2 h at room temperature. The solids were removed by filtration over dicalite and the filtrate was evaporated to dryness. The residue was taken up in 5 mL dichloromethane and 0.072 mL acetic acid and 1.00 g molecular sieve (powder, 4 Å) were added. To the resulting suspension was added 0.536 g sodium triacetoxyborohydride, and the mixture was stirred 1 h at room temperature. Another 0.536 g sodium triacetoxyborohydride was added and the mixture was stirred 1 h. The solids were removed by filtration over dicalite and the filtrate was purified by chromatography on silica gel with 2:1 hexane:ethyl acetate to yield 0.295 g of the tide compound as a yellow solid; melting point 113–114° C. (hexane).

c) (R)-(2-{5-Bromo-2-[dimethyl-(1,1,2-trimethyl-propyl)-silanyloxymethyl]-6-methyl-indol-1-yl}-propyl)-carbamic acid tert-butyl ester To a solution of 0.95 g 5-bromo-2-[dimethyl-(1,1,2-trimethyl-propyl)-silanyloxymethyl]-6-methyl-1H-indole in 10 mL N,N-dimethylformamide was added 0.143 g sodium hydride (55–65%, mineral oil) and the mixture was stirred 30 min at room temperature. To the resulting mixture was added (S)-5-methyl-2,2-dioxo-[1,2,3]oxathiazolidine-3-carboxylic acid tert-butyl ester (0.703 g) and the mixture was stirred 2 h at room temperature. The reaction mixture was partitioned between water and ethyl acetate. The phases were separated and the organic phase was washed with 10% citric acid and brine, dried over magnesium sulfate and purified by chromatography on silica gel with 5:1 hexane-:ethyl acetateto yield 0.789 g of the title compound as a slightly yellow oil. MS: M+H=541.3.

d) 5-Bromo-2-[dimethyl-(1,1,2-trimethyl-propyl)-silanyloxymethyl]-6-methyl-1H-indole To a suspension of 0.5144 g lithium hydroxide in 37 mL dimethylsulfoxide and 3.7 mL water was added 1.800 g (4-bromo-2-{3-[dimethyl-(1,1,2-trimethyl-propyl)-silanyloxy]-prop-1-ynyl}-5-methyl-phenyl)-carbamic acid methyl ester and the mixture was heated 2 h at 80° C. Water and ethyl acetate were added. The pH was adjusted to 6.0 by addition of hydrochloric acid. The phases were separated and the organic phase was washed with 10% sodium bicarbonate and brine and purified by chromatography on silica gel with 9:1 hexane:ethyl acetate to yield 0.97 g of the title compound as a colorless oil. MS: M=383.1.

e) (4-Bromo-2-{3-[dimethyl-(1,1,2-trimethyl-propyl)-silanyloxy]-prop-1-ynyl}-5-methyl-phenyl)-carbamic acid methyl ester To a solution of 3.70 g (4-bromo-2-iodo-5-methyl-phenyl)-carbamic acid methyl ester and 0.070 g bis-triphenylphosphine palladium dichloride and 0.038 g cuprous iodide in 25 mL triethylamine was added 2.38 g dimethyl (2-propynyloxy)(1,1,2-trimethylpropyl)-silane and the mixture was heated 2 h at reflux. The reaction mixture was partitioned between water and ethyl acetate. The phases were separated and the organic phase was washed with 1N hydrochloric acid, sodium bicarbonate and brine, dried with magnesium sulfate and purified by chromatography on silica gel with 4:1 hexane:ethyl acetateto yield 1.92 g of the title compound as a light brown oil. MS: M+NH$_4^+$=457.0 M+Na$^+$=462.2.

f) (4-Bromo-2-iodo-5-methyl-phenyl)-carbamic acid methyl ester

To a solution of 5.00 g (4-bromo-3-methyl-phenyl)-carbamic acid methyl ester in 50 mL acetonitrile were added at 0° C. 4.84 g N-iodosuccinimide and 0.18-mL trifluoromethanesulfonic acid. The mixture was stirred 18 h at room temperature. The solid was collected by filtration, washed with cold acetonitrile and dried to constant weight to yield 5.800 g of the title compound as white crystals melting at 140–141° C.

g) (4-Bromo-3-methyl-phenyl)-carbamic acid methyl ester

To a solution of 10.00 g 4-bromo-3-methylaniline in 50 mL dichloromethane was added 80 mL of a 10% solution of sodium bicarbonate in water. The mixture was cooled to 0° C. and 6.2 mL (7.62 g) methyl chloroformate was added during 10 min. with stirring. The reaction mixture was stirred at room temperature for 1 h. The phases were separated. The organic phase was washed with a 10% solution of citric acid in water, 10% solution of sodium bicarbonate in water and brine, dried with magnesium sulfate and evaporated to yield 12.94 g of the title compound as light brown solid; melting point 71–72° C.

Example 27 a) (R)-4,7-Dimethyl-1,2,3,4-tetrahydro-pyrazino[1,2-a] indole hydrochloride

The title compound (MS: M+H=201.2; mp.: 245° C. (dec)) was produced in accordance with the general method of example 26a) from (R)-4,7-dimethyl-1,2,3,4-tetrahydropyrazino[1,2-a]indole-2-carboxylic acid tert-butyl ester HNMR: (250 MHz, DMSO-d$_6$, δ [ppm]) 1.51 (d, J=6.5 Hz, 3H); 2.43 (s, 3H); 3.50–3.74 (m, 2H); 4.36–4.58 (m, 2H); 4.74–4.89 (m, 1H); 6.34 (s, 1H); 6.82 (d, J=7 Hz, 1H); 7.38 (s, 1H); 7.41 (d, J=7 Hz, 1H).

Intermediate b) (R)-4,7-Dimethyl-1,2,3,4-tetrahydro-pyrazino[1,2-a]indole-2-carboxylic acid tert-butyl ester To a solution of 1.52 g (R)-8-bromo-4,7-dimethyl-1,2,3,4-tetrahydro-pyrazino[1,2-a]indole-2-carboxylic acid tert-butyl ester in 15 ml, ethanol was added 0.15 g 10% palladium on charcoal and the mixture was stirred under a hydrogen atmosphere for 6 h. A further 0.15 g 10% palladium on charcoal was added and the mixture was stirred a further 6 h under a hydrogen atmosphere. Again 0.15 g 10% palladium on charcoal was added and the mixture was stirred a further 6 h under a hydrogen atmosphere. The catalyst was removed by filtration over dicalite and the filtrate was evaporated. The residue was purified by chromatography on silica gel with 4:1 hexane:ethyl acetate to yield 0.59 g of the title compound as a white foam. MS: (M+H)=301.3.

Example 28 a) (R)-4,7,8-Trimethyl-1,2,3,4-tetrahydro-pyrazino[1,2-a]indole

The title compound (MS: M+H=215.3) was produced in accordance with the general method of example 26a) from (R)-4,7,8-trimethyl-1,2,3,4-tetrahydro-pyrazino[1,2-a]indole-2-carboxylic acid tert-butyl ester. The material was isolated as the free amine base by chromatography on silica gel with dichloromethane: methanol: ammonia (9:1:0.1) in the form of a light yellow oil.

HNMR: (250 MHz, CDCl$_3$, δ[ppm]) 1.47 (d, J=6.5 Hz, 3H); 2.33 (s, 3H); 2.38 (s, 3H); 3.07–3.42 (m, 2H); 4.06–4.26 (m, 2H); 4.34–4.42 (m, 1H); 6.02 (s, 1H); 7.07 (s, 1H); 7.31 (s, 1H).

Intermediate b) (R)4,7,8-Trimethyl-1,2,3,4-tetrahydro-pyrazino[1,2-a]indole-2-carboxylic acid tert-butyl ester To a solution of 1.18 g (R)-8-bromo-4,7-dimethyl-1,2,3,4-tetrahydro-pyrazino[1,2a]indole-2-carboxylic acid tert-butyl ester in 12 mL dioxane were added 0.36 g tetrakis(triphenylphosphine)palladium, 1.29 g potassium carbonate and 0.39 trimethylboroxine and the mixture was heated 1 h at reflux. The reaction mixture was partitioned between water and ethyl acetate. The phases were separated and the organic phase was washed with 10% sodium bicarbonate, 10% citric acid and brine, dried over magnesium sulfate and purified by chromatography on silica gel with hexane:ethyl acetate (3:1) to yield 0.62 g of the title compound as slightly yellow foam. MS: (M+H) 315.4.

Example 29 a) (R)-7-Chloro-4,8-dimethyl-1,2,3,4-tetrahydro-pyrazino[1,2-a]indole

The title compound, ISP-MS: m/e=235.2 ([M+H]$^+$), was produced in accordance with the general method of example 1a) from (R)-7-chloro-4,8-dimethyl-3,4-dihydro-2H-pyrazino[1,2-a]indol-1-one. Yellow foam.

Intermediate b) (R)-7-Chloro-4,8-dimethyl-3,4-dihydro-2H-pyrazino[1,2-a]indol-1-one.

The title compound (ISP-MS: m/e=249.2 (M$^+$+H)) was produced in accordance with the general method of example 1b) from 6-chloro-5-methyl-1H-indole-2-carboxylic acid ethyl ester and (S)-5-methyl-2,2-dioxo-[1,2,3]oxathiazolidine-3-carboxylic acid tert-butyl ester. Yield: 34%. Yellow solid.

Intermediate Sulfamidate c) (R,S)-5-Ethyl-2,2-dioxo-[1,2,3]oxathiazolidine-3-carboxylic acid tert-butyl ester The title compound was produced in accordance with the general method of example 1f) from carbamic acid, (2-hydroxybutyl)-, 1,1-dimethylethyl ester (m.p.: 116–118° C.).

Example 30 a) (R)-7,8-Dichloro-4-methyl-1,2,3,4-tetrahydro-pyrazino[1,2-a]indole hydrochloride (R)-7,8-Dichloro-4-methyl-3,4-dihydro-2H-pyrazino[1,2-a]indol-1-one was suspended in toluene and the mixture heated to reflux to remove traces of water. The mixture was cooled to 0° C. (ice-bath) before the addition, via syringe, of borane in tetrahydrofuran. The mixture was stirred 15 min at 0° C., and heated to reflux. After 4 h, the mixture was cooled and excess borane destroyed by the slow addition of a 10% sodium carbonate solution (10 ml). The phases were separated, the aqueous phase extracted with ethyl acetate (2×25 ml), the combined organic phases washed with brine, dried over magnesium sulfate and evaporated. The resulting oil was dissolved in ethyl acetate (5 ml) and a solution of HCl in ethyl acetate added dropwise. The product precipitated out of solution after a short while. It was filtered, washed with a small amount of ethyl acetate and dried to afford the title compound as a white solid (yield 65%).ISP-MS: m/e 255.0 ([M+H]$^+$).

Intermediate b) (R)-7,8-Dichloro-4-methyl-3,4-dihydro-2H-pyrazino[1,2-a]indol-1-one The title compound (EI-MS m/e: 268.1 (M$^+$)) was produced in accordance with the general method of example 1b) from 6,7-dichloro-1H-indole-2-carboxylic acid ethyl ester and (S)-5-methyl-2,2-dioxo-[1,2,3]oxathiazolidine-3-carboxylic acid tert-butyl ester. Yield 67%. Light orange solid.

Example 31 a) (R)-4-Methyl-6-trifluoromethyl-1,2,3,4-tetrahydro-pyrazino[1,2-a]indole hydrochloride The title compound (ISP-MS m/e: 255.3 ([M+H]$^+$)) was produced in accordance with the general method of example 1a) from (R)-4-Methyl-6-trifluoromethyl-3,4-dihydro-2H-pyrazino[1,2-a]indol-1-one.

Intermediate b) (R)-4-Methyl-6-trifluoromethyl-3,4-dihydro-2H-pyrazino[1,2-a]indol-1-one The title compound was produced in accordance with the general method of example 1b) from 7-trifluoromethyl-1H-indole-2-carboxylic acid ethyl ester and (S)-5-methyl-2,2-dioxo-[1,2,3]oxathiazolidine-3-carboxylic acid tert-butyl ester. Yield 8%. Off-white solid.

Example 32 a) (R)-7-fluoro-4,6-dimethyl-1,2,3,4-tetrahydro-pyrazino[1,2-a]indole

The title compound (EI-MS m/e: 218.1 (M$^+$)) was produced in accordance with the general method of example 1a) from (R)-7-fluoro-4,6-dimethyl-3,4-dihydro-2H-pyrazino[1,2-a]indol-1-one. Off-white solid. Yield: 79%.

Intermediates
b) (R)-7-fluoro-4,6-dimethyl-3,4-dihydro-2H-pyrazino[1,2-a]indol-1-one The title compound (ISP-MS m/e: 233.1 ([M+H]$^+$)) was produced in accordance with the general method of example 1b) from 6-fluoro-7-methyl-1H-indole-2-carboxylic acid ethyl ester and (S)-5-methyl-2,2-dioxo-[1,2,3] oxathiazolidine-3-carboxylic acid tert-butyl ester. Yield 7%. White solid.

c) 6-Fluoro-7-methyl-1H-indole-2-carboxylic acid ethyl ester

A mixture of 7.6 g (E)/(Z)-2-[(3-fluoro-2-methyl-phenyl)-hydrazono]-propionic acid ethyl ester and 8.2 g p-toluenesulfonic acid (dried by azeotropic distillation with toluene) was heated 1 h at reflux in toluene. The solution was cooled, poured into half-saturated aqueous sodium bicarbonate solution, and the aqueous phase extracted twice with ethyl acetate. The combined organic phases were washed with brine, dried over sodium sulfate and evaporated. The residue was purified by column chromatography on silica gel (8:1 to 6:1 hexane/ethyl acetate eluant) to afford the title compound as a light brown solid, (24% yield, mp 149° C.; EI-MS m/e: 221.1 (M$^+$))

d) (E) and (Z)-2-[(3-fluoro-2-methyl-phenyl)-hydrazono]-propionic acid ethyl ester To a cooled (ice-bath) solution of (3-fluoro-2-methyl-phenyl)-hydrazine (8.4 g) in ethanol was added ethyl pyruvate. The solution was stirred overnight at room temperature and evaporated. The residue was triturated with hexane. The precipitate that formed was collected by filtration and dried under vacuum to afford the title compound as an off-white solid (9.1 g, 64% yield; EI-MS m/e: 238.1 (M$^+$))

e) (3-Fluoro-2-methyl-phenyl)-hydrazine 24 g 3-Fluoro-2-methyl-aniline was added to 120 ml 25% hydrochloric acid and the mixture cooled to 0° C. A solution of 15 g sodium nitrite in 80 ml water was added dropwise to the resulting suspension at such a rate that the temperature did not rise above 8° C. When the addition was complete, the mixture was stirred 1 h at 0° C. Whilst maintaining the mixture at 0° C., a suspension of 195 g tin (II) chloride in 230 ml 25% aqueous hydrochloric acid was added over 30 min. The mixture was stirred a further 20 min, and the precipitate that formed was filtered. The crude hydrochloride salt was partitioned between water and dichloromethane, and the pH raised to pH8 by the addition of sodium hydroxide solution followed by saturated sodium bicarbonate solution. The phases were separated, the aqueous phase extracted twice with dichloromethane and the combined organic phases dried over sodium sulfate and evaporated. The resulting solid residue was recrystallised from hexane to afford the title compound as a light brown solid (9.2 g, 34% yield, mp 69° C.; EI-MS m/e: 140.1 (M$^+$)).

Example 33
a) (R)-6-bromo-8-fluoro-4-methyl-1,2,3,4-tetrahydropyrazino[1,2-a]indole The title compound (ISP-MS: m/e 283.0 ([M+H]$^+$) was produced in accordance with the general method of example 1a) from JR)-6-bromo-8-fluoro-4-methyl-3,4-dihydro-2H-pyrazino[1,2-a]indol-1-one, along with 8-fluoro-4-methyl-1,2,3,4-tetrahydro-pyrazino[1,2-a]indole. The mixture of compounds (196 mg) was dissolved in N,N-dimethylformamide and triethylamine and di-tert-butyl-dicarbonate added. The mixture was stirred 5 h at room temperature, diluted with ethyl acetate, washed with water, brine and dried over magnesium sulfate. The solvent was evaporated and the residue purified by column chromatography on silica gel to afford 6-bromo-8-fluoro-4-methyl-3,4-dihydro-1H-pyrazino[1,2-a]indole-2-carboxylic acid tert-butyl ester as a pale yellow oil which was dissolved in dichloromethane and trifluoroacetic acid at 0° C. The mixture was stirred 1 h at 0° C., evaporated to dryness, and the residue taken up in dichloromethane, washed with aqueous sodium bicarbonate solution, water, dried over magnesium sulfate and evaporated. The residue was purified by column chromatography on silica gel to afford the title compound as a yellow oil. Yield 44%.

Intermediates
b) (R)-6-bromo-8-fluoro-4-methyl-3,4-dihydro-2H-pyrazino[1,2-a]indol-1-one The title compound (ISP-MS m/e: 297.2 (M+H)$^+$) was produced in accordance with the general method of example 1b) from 7-bromo-5-fluoro-1H-indole-2-carboxylic acid ethyl ester and (S)-5-methyl-2,2-dioxo-1,2,3] oxathiazolidine-3-carboxylic acid tert-butyl ester. Yield 56%. Off-white solid.

c) 7-bromo-5-fluoro-1H-indole-2-carboxylic acid ethyl ester 57 g (E)-2-[(2-Bromo-4-fluoro-phenyl)-hydrazono]-propionic acid ethyl ester was dissolved in 600 ml Eaton's reagent and heated 3 h at 50° C. The cooled mixture was diluted with dichloromethane and poured into a saturated aqueous sodium bicarbonate solution. The phases were separated, the aqueous phase extracted with dichloromethane and the combined organic phases washed with water, dried over sodium sulfate and evaporated. The residue was purified by column chromatography on silica gel (5:1 to 1:0 toluene/hexane eluant) to afford the title compound as a yellow solid. EI-MS m/e: 285.0 ([M+H]$^+$). Yield: 28.6 g.

d) (E)-2-[(2-Bromo-4-fluoro-phenyl)-hydrazono]-propionic acid ethyl ester

To a cooled (ice-bath) suspension of 126 g 5-(2-Bromo-4-fluoro-phenylazo)-2,2,5-trimethyl-[1,3]dioxane-4,6-dione in 550 ml ethanol was added a solution of 7.8 g sodium in 200 ml ethanol. The mixture was stirred 5 h at room temperature, poured into 200 ml water and the organics extracted with ethyl acetate. The combined organic phases were washed with brine, dried over magnesium sulfate and evaporated. The resulting orange oil solidified upon drying under vacuum to afford the title compound. Yield:102 g. ISP-MS: m/e 303.2 ([M+H]$^+$).

e) 5-(2-Bromo-4-fluoro-phenylazo)-2,2,5-trimethyl-[1,3] dioxane-4,6-dione 130 g 2-Bromo-4-fluoro-aniline was dissolved in 700 ml ice and 600 ml 3M hydrochloric acid. The resulting suspension was maintained at ca. 5° C. during the addition of a solution of 47.3 g sodium nitrite in 45 ml water. When the addition was complete, the mixture was stirred 45 min at ca 5° C. The resulting brown suspension was added slowly to a cooled mixture of 108.3 g 2,2,5-trimethyl-1,3-dioxan-4,6-dione and 932 g sodium acetate in 400 ml water and 700 ml ethanol, maintaining the temperature between 3 and 8° C. A yellow precipitate formed. The mixture was stirred a further 2 h at 3–8° C., filtered and the precipitate washed with water and dried under vacuum to afford the title compound as a yellow solid. ISP-MS: m/e 359 ([M+H]$^+$). Yield 231 g, mp 92–93° C.

Example 34
a) (R)-8-fluoro-4,6-dimethyl-1,2,3,4-tetrahydro-pyrazino[1,2-a]indole hydrochloride The tide compound (ISP-MS: m/e 219.3 ([M+H]$^+$)) was produced in accordance with the general method of example 1a), using tert-butyl-methyl ether instead of tetrahydrofuran as solvent, from (R)-8-fluoro-4,6-dimethyl-3,4-dihydro-2H-pyrazino[1,2-a]indol-1-one. The product (20 mg) was dissolved in dichloromethane and treated with a solution of HCl in diethyl ether to precipitate the hydrochloride salt Yield: 18 mg.

Intermediate b) (R)-8-fluoro-4,6-dimethyl-3,4-dihydro-2H-pyrazino[1,2-a]indol-1-one 1.2 g (R)-6-bromo-8-fluoro-4-methyl-3,4-dihydro-2H-pyrazino[1,2-a]indol-1-one was dissolved in 12 ml N,N-dimethylformamide under argon. 0.45 gTetrakis-(triphenylphosphine)palladium, 1.56 g potassium carbonate and 0.55 ml trimethylboroxine were added. The mixture was heated overnight at 110° C., allowed to cool to room temperature, filtered over dicalite and washed through with tetrahydrofuran. The solvents were evaporated under reduced pressure and the residue purified by column chromatography on silica gel (1:1 to 1:3 toluene/ethyl acetate) to afford the title product as an off-white solid. Yield: 300 mg ISP-MS: m/e 233.1 ([M+H]$^+$).

Example 35 a) (R)-6-Ethyl-8-fluoro-4-methyl-1,2,3,4-tetrahydro-pyrazino[1,2-a]indole hydrochloride The title compound (ISP-MS: m/e 233.3 ([M+H]$^+$)) was produced in accordance with the general method of example 1a), using tert-butyl-methyl ether instead of tetrahydrofuran as solvent, from (R)-6-ethyl-8-fluoro-4-methyl-3,4-dihydro-2H-pyrazino[1,2-a]indol-1-one. The product was dissolved in dichloromethane and treated with a solution of HCl in diethyl ether to precipitate the hydrochloride salt. Yield: 62%. Off-white solid.

Intermediates b) (R)-6-Ethyl-8-fluoro-4-methyl-3,4-dihydro-2H-pyrazino [1,2-a]indol-1-one 6.2 g (R)-6-bromo-8-fluoro-4-methyl-3,4-dihydro-2H-pyrazino[1,2-a]indol-1-one was dissolved in 150 ml N,N-dimethylformamide under argon. 1.43 g (Dppf)PdCl$_2$, 39 g caesium carbonate and 41.6 ml of a 1M solution of triethylborane in tetrahydrofuran were added. The mixture was heated 15 h at 50° C., allowed to cool to room temperature and poured into water. The aqueous mixture was extracted with ethyl acetate. The combined organic phases washed with brine, dried over magnesium sulfate and evaporated. The residue was purified by column chromatography on reversed phase silica gel (6:4 to 3:7 water/methanol) to afford the title product as an off-white solid. Yield: 1.8 g. ISP-MS: m/e 247.3 ([M+H]$^+$).

Example 36 a) (R)-7-Chloro-4,10-dimethyl-1,2,3,4-tetrahydro-pyrazino [1,2-a]indole oxalate

The title compound (EI-MS: m/e=234.1 ([M-C$_2$H$_2$O$_4$)$^+$)) was produced in accordance with the general method of example 14a) from (R)-7-chloro-4-methyl-3,4-dihydro-2H-pyrazino[1,2-a]indol-1-one. Light yellow solid.

Intermediates b) (R)-7-Chloro-4,10-dimethyl-3,4-dihydro-2H-pyrazino[1, 2-a]indol-1-one The title compound (ISP-MS: m/e=249.2 ([M+H]$^+$)) was produced in accordance with the general method of example 1b) from 6-chloro-3-methyl-1H-indole-2-carboxylic acid ethyl ester and (S)-5-methyl-2,2-dioxo-[1,2,3] oxathiazolidine-3-carboxylic acid tert-butyl ester. White solid.

c) 6-Chloro-3-methylindole-1H-indole-2 carboxylic acid ethyl ester

A solution of sodium nitrite (5.95 g, 86.2 mmol) in water (7 mL) was added dropwise at –5° C. to a mixture of 3-chloroaniline (10.0 g, 78.4 mmol) in water (27 mL) and 37% aq. hydrochloric acid solution (16 mL), then after 15 min sodium acetate (5.47 g, 66.6 mmol) was added. In a separate flask a solution of ethyl α-ethylacetoacetate (13.6 g, 86.2 mmol) in ethanol (50 mL) was treated with with a solution of 85% potassium hydroxide (5.69 g, 86.2 mmol) in water (6 mL) at 0° C., then ice (80 g) and the above prepared aryldiazonium solution were rapidly added. The two-phase mixture obtained was stirred 3 h at 0° C., and kept at 4° C. overnight, then extracted with ethyl acetate (2×200 mL). The organic layer was washed with brine, dried (MgSO$_4$), and evaporated. The resultant red oil was added within 30 min to a boiling mixture of ethanol (100 mL) and acetyl chloride (25 mL). After 2 h at reflux, the mixture was cooled to room temperature then filtered. The filtrate was evaporated then partitioned between water and chloroform. The organic layer was washed with sat. aq. sodium hydrogen carbonate solution and brine, dried (MgSO$_4$), and evaporated. The solid was successively triturated in dichloromethane/hexane 1:1 (100 mL) and ether (50 mL, twice) to afford the title compound (4.06 g, 22%). White solid, EI-MS: m/e=237.1 (M$^+$).

Example 37 a) (R)-6,7-Dichloro-4-methyl-1,2,3,4-tetrahydro-pyrazino [1,2-a]indole hydrochloride The title compound (ISP-MS: m/e=255.1 ([MH–Cl]$^+$)) was produced in accordance with the general method of example 17a) from (R)-7-chloro-4-methyl-3,4-dihydro-2H-pyrazino[1,2-a]indol-1-one and isolated as the hydrochloride salt. White solid.

Intermediate b) (R)-6,7-Dichloro-4,10-dimethyl-3,4-dihydro-2H-pyrazino[1,2-a]indol-1-one The title compound (ISP-MS: m/e=269.2 ([M+H])) was produced in accordance with the general method of example 1b) from 6,7-dichloro-3-methyl-1H-indole-2-carboxylic acid ethyl ester and (S)-5-methyl-2,2-dioxo-[1,2,3] oxathiazolidine-3-carboxylic acid tert-butyl ester. White solid.

Example 38 a) (R)-10-Ethoxy-4,6-dimethyl-1,2,3,4-tetrahydro-pyrazino [1,2-a]indole hydrochloride The title compound (ISP-MS: m/e=245.3 ([MH–Cl]$^+$)) was produced in accordance with the general method of example 17a) from (R)-10-ethoxy-4,6-dimethyl-3,4-dihydro-2H-pyrazino[1,2-a]indol-1-one and isolated as the hydrochloride salt. White solid.

Intermediates b) (R)-10-Ethoxy-4,6-dimethyl-3,4-dihydro-2H-pyrazino[1, 2-a]indol-1-one The title compound (ISP-MS: m/e=259.1 ([M+H]$^+$)) was produced in accordance with the general method of example 1a) from 3-ethoxy-7-methyl-1H-indole-2-carboxylic acid ethyl ester and (S)-5-methyl-2,2-dioxo-[1,2,3] oxathiazolidine-3-carboxylic acid tert-butyl ester. Light yellow foam.

c) 3-Ethoxy-7-methyl-1H-indole-2-carboxylic acid ethyl ester

Toluene-4-sulfonic acid ethyl ester (274 mg, 1.37 mmol) and potassium carbonate (378 mg, 2.74 mmol) were added to a solution of 3-hydroxy-7-methyl-1H-indole-2-carboxylic acid ethyl ester (300 mg, 1.37 mmol) in N,N-dimethylformamide (3 mL). The mixture was stirred at 50° C. for 16 h, then cooled to room temperature and partitioned between ethyl acetate and water. The organic layer was separated, washed with brine, dried ($MgSO_4$), and evaporated. Chromatography ($SiO_2$, hexane/ethyl acetate 6:1) afforded the title compound (250 mg, 74%). White solid, ISP-MS: m/e=248.2 ([M+H$^+$]).

Example 39 a) (R)-10-Methoxy-4,6-dimethyl-1,2,3,4-tetrahydro-pyrazino[1,2-a]indole

The title compound (ISP-MS: m/e=231.2 ([M+H]$^+$)) was produced in accordance with the general method of example 17a) from (R)-10-methoxy-4,6-dimethyl-3,4-dihydro-2H-pyrazino[1,2-a]indol-1-one. Yellow oil.

Intermediates b) (R)-10-Methoxy-4,6-dimethyl-3,4-dihydro-2H-pyrazino[1,2-a]indol-1-one The title compound (ISP-MS: m/e=245.3 ([M+H$^+$])) was produced in accordance with the general method of example 1b) from 3-methoxy-7-methyl-1H-indole-2-carboxylic acid ethyl ester and (S)-5-methyl-2,2-dioxo-[1,2,3]oxathiazolidine-3-carboxylic acid tert-butyl ester. Light yellow foam.

c) 3-Methoxy-7-methyl-1H-indole-2-carboxylic acid ethyl ester

The title compound (EI-MS: m/e=233.2 (M$^+$)) was produced in accordance with the general method of example 38c) from 3-hydroxy-7-methyl-1H-indole-2-carboxylic acid ethyl ester and toluene-4-sulfonic acid methyl ester. Off-white solid.

Example 40 a) (R)-4,7,9-Trimethyl-1,2,3,4-tetrahydro-pyrazino[1,2-a]indole

The title compound (ISP-MS: m/e=215.4 ([M+H$^+$])) was produced in accordance with the general method of example 17a) from (R)-4,7,9-trimethyl-3,4-dihydro-2H-pyrazino[1,2-a]indol-1-one. Light yellow solid.

Intermediate b) (R)-4,7,9-Trimethyl-3,4-dihydro-2H-pyrazino[1,2-a]indol-1-one

The title compound (EI-MS: m/e=228.3 ([M])) was produced in accordance with the general method of example 1b) from 4,6-dimethyl-1H-indole-2-carboxylic acid ethyl ester and (S)-5-methyl-2,2-dioxo-[1,2,3]oxathiazolidine-3-carboxylic acid tert-butyl ester. Colorless solid.

Example 41 a) (R)-6-Bromo-4-methyl-1,2,3,4-tetrahydro-pyrazino[1,2-a]indole hydrochloride

The title compound (EI-MS: m/e=264.1 ([M])) was produced in accordance with the general method of example 17a) from (R)-6-bromo-4-methyl-3,4-dihydro-2H-pyrazino[1,2-a]indol-1-one. The free base was dissolved in 3 ml ethyl acetate and treated dropwise with 0.30 ml of a 6M hydrochloric acid solution in ethyl acetate. The resulting suspension was stirred for 30 min., filtered and the solid was washed with ethyl acetate and dried under high vacuum to give the desired compound as an off-white solid.

Intermediates b) (R)-6-Bromo-4-methyl-3,4-dihydro-2H-pyrazino[1,2-a]indol-1-one

A solution of 6.10 g (14.3 mmol) (R)-7-bromo-1-(2-tert-butoxycarbonylamino-1-methyl-ethyl)-1H-indole-2-carboxylic acid ethyl ester in 65 ml dichloromethane was cooled down to 0° C. and treated dropwise with 32 ml (28.7 mmol) trifluoroacetic acid. The cooling bath was removed and after 45 min. stirring at room temperature all volatile components were removed at a rotary evaporator and the remaining oil was dissolved in 35 ml methanol. To this solution, 7.93 g (57.4 mmol) potassium carbonate was added and the reaction was stirred for 16 h. The suspension was poured onto water and ethyl acetate; the organic layer was washed with water, dried over magnesium sulfate, filtered and evaporated. The residue was dissolved in dichloromethane, tert-butyl methyl ether was added and the solution was concentrated at a rotary evaporator until a white precipitate began to form. The suspension was filtered, the solid material was washed with tert-butyl methyl ether and dried under high vacuum to give the desired compound as white crystalline solid. ISP-MS: m/e=2381.1 ([M+H+1]).

c) (R)-7-Bromo-1-(2-tert-butoxycarbonylamino-1-methyl-ethyl)-1H-indole-2-carboxylic acid ethyl ester A solution of 8.1 g (30.1 mmol) 7-bromo-1H-indole-2-carboxylic acid ethyl ester in 120 ml N,N-dimethylformamide was cooled to 0° C. and 3.55 g (31.6 mmol) potassium tert-butoxide was added. After 30 min., 7.86 g (33.1 mmol) (S)-5-methyl-2,2-dioxo-[1,2,3]oxathiazolidine-3-carboxylic acid tert-butyl ester were added and the cooling bath was removed. After 20 h the reaction mixture was poured on 10% aqueous citric acid solution and ethyl acetate. The organic layer was dried over magnesium sulfate, filtered and evaporated. The resulting yellow oil was chromatographed on silica gel (0.032–0.063 mm) with tert-butyl methyl ether: n-hexane (1:8) as eluant to give the desired compound as a yellow oil. ISP-MS: m/e=427.3 ([M+H$^+$]).

Example 42 a) (R)-8-Fluoro-4,7-dimethyl-1,2,3,4-tetrahydro-pyrazino[1,2-a]indole hydrochloride The title compound (EI-MS: m/e=218.1 ([M])) was produced in accordance with the general method of example 41a) from (R)-8-fluoro-4,7-dimethyl-1,2,3,4-tetrahydro-pyrazino[1,2-a]indole. Off-white solid. Found: C, 61.17; H. 6.54; Cl, 13.65; F, 7.20; N, 10.83. $C_{13}H_{16}ClFN_2$ requires C, 61.30; H, 6.33; Cl, 13.92; F, 7.46; N. 11.00%.

Intermediates b) (R)-8-Fluoro-4,7-dimethyl-1,2,3,4-tetrahydro-pyrazino[1,2-a]indole The title compound (EI-MS: m/e=218.1 ([M])) was produced in accordance with the general method of example 17a) from (R)-8-fluoro-4,7-dimethyl-3,4-dihydro-2H-pyrazino[1,2-a]indol-1-one. Light brown solid.

c) (R)-8-Fluoro-4,7-dimethyl-3,4-dihydro-2H-pyrazino[1,2-a]indol-1-one

The title compound (EI-MS: m/e=232.1 ([M])) was produced in accordance with the general method of example 1b) from 5-fluoro-6-methyl-1H-indole-2-carboxylic acid ethyl ester and (S)-5-methyl-2,2-dioxo-[1,2,3]oxathiazolidine-3-carboxylic acid tert-butyl ester. Colorless solid.

Example 43 a) (R)-6-Fluoro-4,7-dimethyl-1,2,3,4-tetrahydro-pyrazino[1,2-a]indole hydrochloride The title compound (EI-MS: m/e=218.1 ([M])) was produced in accordance with the general method of example 41a) from (R)-6-fluoro-4,7-dimethyl-1,2,3,4-tetrahydro-pyrazino[1,2-a]indole. Colorless solid.

Intermediates b) (R)-6-Fluoro-4,7-dimethyl-1,2,3,4-tetrahydro-pyrazino(1,2-a]indole The title compound (EI-MS: m/e=218.1 ([M])) was produced in accordance with the general method of example 17a) from (R)-6-fluoro-4,7-dimethyl-3,4-dihydro-2H-pyrazino[1,2-a]indol-1-one. Light brown solid.

c) (R)-6-Fluoro-4,7-dimethyl-3,4-dihydro-2H-pyrazino[1,2-a]indol-1-one

The title compound (EI-MS: m/e=232.1 ([M])) was produced in accordance with the general method of example 1b) from 5-fluoro-6-methyl-1H-indole-2-carboxylic acid ethyl ester and (S)-5-methyl-2,2-dioxo-[1,2,3]oxathiazolidine-3-carboxylic acid tert-butyl ester. Colorless solid.

Example 44 a) (R)-4-Methyl-1,2,3,4-tetrahydro-pyrazino[1,2-a]indole-6-carbonitrile hydrochloride A solution of 80.0 mg (0.26 mmol) 6-cyano-4-methyl-3,4-dihydro-1H-pyrazino[1,2-a]indole-2-carboxylic acid tert-butyl ester in 3 ml dichloromethane was cooled to 0° C. and treated dropwise with 1 ml trifluoroacetic acid. After 30 min. the solution was concentrated at a rotary evaporator and the residue was chromatographed on silica gel (0.032–0.063 mm) with ethyl acetate: methanol: ammonia (9:1:0.1) as eluant. The product was dissolved in 3 ml diethyl ether and treated dropwise with 43 µl of a 6M hydrochloric acid solution in ethyl acetate. The suspension was filtered and the solid was dried under high vacuum to give the desired compound as light yellow crystals. EI-MS:: m/e=211.2 ([M]).

Intermediates b) 6-Bromo-4-methyl-3,4-dihydro-1H-pyrazino[1,2-a]indole-2-carboxylic acid tert-butyl ester To a solution of 1.0 g (3.77 mmol) 6-bromo-4-methyl-1,2,3,4-tetrahydro-pyrazino[1,2-a]indole in 10 ml dichloromethane was added 0.99 g (4.53 mmol) di-tert-butyldicarbonate. The solution was stirred for 1 h at room temperature, the solvent was removed at a rotary evaporator and the residue was chromatographed on silica gel (0.032–0.063 mm) with n-hexane:ethyl acetate (9:1) as eluant to give the compound as a light yellow foam. EI-MS: m/e=307.1 ([M]).

c) 6-Cyanomethyl-3,4-dihydro-1H-pyrazino[1,2-a]indole-2-carboxylic acid tert-butyl ester A suspension of 0.30 g (0.82 mmol) 6-bromo-4-methyl-3,4-dihydro-1H-pyrazino[1,2-a]indole-2-carboxylic acid tert-butyl ester, 0.29 g (3.3 mmol) copper(I)cyanide, 34.0 mg (0.030 mmol) tris(dibenzylideneacetone)dipalladium(0), 72.9 mg (0.013 mmol) 1,1'-bis(diphenylphosphino) ferrocene and 128.3 mg (0.82 mmol) tetraethylammonium cyanide in 6 ml dioxane was heated under reflux for 18 h. The reaction mixture was filtered, diluted with ethyl acetate and extracted with 10% aqueous citric acid, 10% aqueous sodium bicarbonate solution and brine. After drying over magnesium sulfate and filtration, the solvent was removed at a rotary evaporator and the residue was purified by chromatography on silica gel (0.032–0.063 mm) with n-hexane:ethyl acetate (9:1) as eluant to give the product as a light yellow foam. ISP-MS: m/e 312.2 ([M+H$^+$]).

Example 45 a) 6-Chloro-4,8-dimethyl-1,2,3,4-tetrahydro-pyrazino[1,2-a]indole hydrochloride

The title compound (ISP-MS: m/e=235.3 ([M+H$^+$])) was produced in accordance with the general method of example 41a) from 6-chloro-4,8-dimethyl-1,2,3,4-tetrahydro-pyrazino[1,2-a]indole. White crystalline solid.

Intermediates b) 6-Chloro-4,8-dimethyl-1,2,3,4-tetrahydro-pyrazino[1,2-a]indole

The title compound (ISP-MS: m/e=235.3 ([M+H$^+$])) was produced in accordance with the general method of example 17a) from 6-chloro-4,8-dimethyl-3,4-dihydro-2H-pyrazino[1,2-a]indol-1-one. White crystalline solid.

c) 6-Chloro-4,8-dimethyl-3,4-dihydro-2H-pyrazino[1,2-a]indol-1-one

The title compound (EI-MS: m/e=248.2 ([M])) was produced in accordance with the general method of example 41b) from 6-chloro-4,8-dimethyl-3,4-dihydro-2H-pyrazino[1,2-a]indol-1-one. White crystalline solid.

d) 1-(2-tert-Butoxycarbonylamino-1-methyl-ethyl)-7-chloro-5-methyl-1H-indole-2-carboxylic acid ethyl ester The title compound (EI-MS: m/e=394.3 ([M])) was produced in accordance with the general method of example 41c) from 7-chloro-5-methyl-1H-indole-2-carboxylic acid ethyl ester and (S)-5-methyl-2,2-dioxo-[1,2,3]oxathiazolidine-3-carboxylic acid tert-butyl ester. Colorless oil.

Example 46 a) 6-Fluoro-4,9-dimethyl-1,2,3,4-tetrahydro-pyrazino[1,2-a]indole hydrochloride

The title compound (ISP-MS: m/e=219.3 ([M+H$^+$])) was produced in accordance with the general method of example 41a) from 6-fluoro-4,9-dimethyl-1,2,3,4-tetrahydro-pyrazino[1,2-a]indole. White crystalline solid.

Intermediates b) 6-Fluoro-4,9-dimethyl-1,2,3,4-tetrahydro-pyrazino[1,2-a]indole

The title compound (ISP-MS: m/e=219.3 ([M+H$^+$])) was produced in accordance with the general method of example 17a) from 6-fluoro-4,9-dimethyl-3,4-dihydro-2H-pyrazino[1,2-a]indol-1-one. Light yellow solid.

c) 6-Fluoro-4,9-dimethyl-3,4-dihydro-2H-pyrazino[1,2-a]indol-1-one

The title compound (EI-MS: m/e=232.2 ([M])) was produced in accordance with the general method of example 17b) from 7-fluoro-4-methyl-1H-indole-2-carboxylic acid ethyl ester and (S)-5-methyl-2,2-dioxo-[1,2,3]oxathiazolidine-3-carboxylic acid tert-butyl ester. Light yellow crystalline solid.

Example 47 a) (R)-6-Bromo-4,7-dimethyl-1,2,3,4-tetrahydro-pyrazino[1,2-a]indole; hydrochloride The title compound (ISP-MS: m/e=281.1 ([M+H$^+$])) was produced in accordance with the general method of example 41a) from (R)-6-bromo-4,7-dimethyl-1,2,3,4-tetrahydro-pyrazino[1,2-a]indole. Light yellow crystalline solid.

Intermediates b) (R)-6-Bromo-4,7-dimethyl-1,2,3,4-tetrahydro-pyrazino[1,2-a]indole The title compound (ISP-MS: m/e=279.1 ([M+H$^+$])) was produced in accordance with the general method of example 17a) from (R)-6-bromo-4,7-dimethyl-3,4-dihydro-2H-pyrazino[1,2-a]indol-1-one. Light yellow oil.

c) (R)-6-Bromo-4,7-dimethyl-3,4-dihydro-2H-pyrazino[1,2-a]indol-1-one

The title compound (ISP-MS: m/e=293.2 ([M+H$^+$])) was produced in accordance with the general method of example 41b) from 7-bromo-1-(2-tert-butoxycarbonylamino-1-methyl-ethyl)-6-methyl-1H-indole-2-carboxylic acid ethyl ester. Beige solid.

d) 7-Bromo-1-(2-tert-butoxycarbonylamino-1-methyl-ethyl)-6-methyl-1H-indole-2-carboxylic acid ethyl ester The title compound (ISP-MS: m/e=441.3 ([M+H$^+$])) was produced in accordance with the general method of example 41c) from 7-bromo-6-methyl-1H-indole-2-carboxylic acid ethyl ester and (S)-5-methyl-2,2-dioxo-[1,2,3]oxathiazolidine-3-carboxylic acid tert-butyl ester. Light yellow oil.

Example 48 a) (R)-6-chloro-4,7-dimethyl-1,2,3,4-tetrahydro-pyrazino[1,2-a]indole

The title compound (EI-MS m/e: 234.1 (M$^+$)) was produced in accordance with the general method of example 1a) from (R)-6-chloro-4,7-dimethyl-3,4-dihydro-2H-pyrazino[1,2-a]indol-1-one. Light yellow solid. Yield: 74%. Mp:103–105° C.

Intermediates b) (R)-6-chloro-4,7-dimethyl-3,4-dihydro-2H-pyrazino[1,2-a) indol-1-one The title compound (ISP-MS m/e: 249.2 ([M+H]$^+$)) was produced in accordance with the general method of example 1b) from 7-chloro-6-methyl-1H-indole-2-carboxylic acid ethyl ester and (S)-5-methyl-2,2-dioxo-[1,2,3]oxathiazolidine-3-carboxylic acid tert-butyl ester. Yield 72%. Light brown resin.

c) 7-Chloro-6-methyl-1H-indole-2-carboxylic acid ethyl ester

The title compound (EI-MS m/e: 237.1 ([M+])) was produced in accordance with the general method of example 32c) from a mixture of (E) and (Z)-2-[(2-chloro-3-methyl-phenyl)-hydrazono]-propionic acid ethyl ester. Yellow solid. Yield: 67%, mp 73–75° C.

d) (E) and (Z)-2-[(2-chloro-3-methyl-phenyl)-hydrazono]-propionic acid ethyl ester The title compound (EI-MS m/e: 254.1 ([M]+)) was produced in accordance with the general method of example 32d) from (2-chloro-3-methyl-phenyl)-hydrazine. Yellow solid. Yield: 91%.

Example 49 a) (R)-10-Methyl-2,3,7,8,9,10-hexahydro-1H-8,10a-diaza-cyclopenta[c]fluorene hydrochloride (R)-10-Methyl-2,3,9,10-tetrahydro-1H,8H-8,10a-diaza-cyclopenta[c]fluoren-7-one (0.45 g; 2 mmol) was dissolved in diethylether (200 mL) and lithium aluminium hydride (0.15 g, 4 mmol) was added in portions with cooling. The solution was stirred for 2 h under reflux, cooled and hydrolysed by sequential addition of water (0.6 mL), sodium hydroxide solution (15%, 1.2 mL) and water (1.2 mL). Diethyl ether was added (100 mL), the mixture was filtered and the filtrate evaporated. The residue was stirred with hexane (20 mL) and diethylether (1 mL) to give the title compound as white solid; ISP-MS: m/e=227.2 (M+H$^+$), and crystallised as HCl salt. $\alpha_D^{20}$=−210.2.

Intermediates b) (R)-10-Methyl-2,3,9,10-tetrahydro-1H,8H-8,10a-diaza-cyclopenta[c]fluoren-7-one (R)-1-(2-tert-Butoxycarbonylamino-1-methyl-ethyl)-1,6,7,8-tetrahydro-1-aza-as-indacene-2-carboxylic acid ethyl ester (7.2 g, ~17 mmol) was dissolved in dichloromethane (110 mL) and treated with trifluoroacetic acid (29 mL) at 0° C. After removal of the ice bath, the solution was stirred for 1 h, and evaporated under reduced pressure. The residue was dissolved in methanol (120 mL); after addition of saturated sodium bicarbonate solution (110 mL) and 2.6 g potassium carbonate the mixture was stirred for 20 h at room temperature. Water (100 mL) was added and the mixture was extracted with dichloromethane (2×100 mL). The organic layer was separated, washed with brine, dried (MgSO$_4$), and evaporated. Crystallization from diethyl ether yielded the title compound as a colorless solid (2.6 g, 57%). EI-MS: m/e 240.2 (M$^+$).

c) (R)-1-(2-tert-Butoxycarbonylamino-1-methyl-ethyl)-1,6,7,8-tetrahydro-1-aza-as-indacene-2-carboxylic acid ethyl ester Sodium hydride (0.91 g, 21 mmol) was suspended in N,N-dimethylformamide (25 mL) and a solution of 1,6,7,8-tetrahydro-1-aza-indacene-2-carboxylic acid ethyl ester (4.0 g, 17 mmol) in N,N-dimethylformamide (25 mL) was added with cooling at 5° C. After 1 h (S)-5-methyl-2,2-dioxo-[1,2,3]oxathiazolidine-3-carboxylic acid tert-butyl ester (5.0 g, 21 mmol) was added and the solution was allowed to reach room temperature overnight. The solution was partitioned between ice water (1000 mL) and diethyl ether (2×250 mL). The organic layer was washed with ice water and brine, dried (MgSO$_4$), and evaporated. The product was used without further purification (7.2 g). EI-MS: m/e=386.2 (M$^+$).

d) 1,6,7,8-Tetrahydro-1-aza-as-indacene-2-carboxylic acid ethyl ester

The title compound, EI-MS: m/e=229.21 (M$^+$), was prepared in accordance with the general method of example 32c) from 2-[((2,3-Dihydro-1H-inden-4-yl)-hydrazono]-propionic acid ethyl ester. Yellow solid. Yield 98%.

e) 2-[((2,3-Dihydro-1H-inden-4-yl)-hydrazono]-propionic acid ethyl ester

The title compound, ISP-MS: m/e=247.3 (M+H$^+$), was prepared in accordance with the general method of example 32d), using dichloromethane as solvent, from (2,3-Dihydro-1H-inden-4-yl)-hydrazine and ethyl pyruvate. Brown solid. Yield 86%.

Example 50 a) (R)-7-Bromo-4,6-dimethyl-1,2,3,4-tetrahydro-pyrazino[1,2-a]indole

The title compound, ISP-MS: m/e=279.1, 281.1 (M+H$^+$), was prepared in accordance with the general method of example 49a) from (R)-7-bromo-4,6-dimethyl-3,4-dihydro-2H-pyrazino[1,2-a]indol-1-one.

Intermediates b) (R)-7-Bromo-4,6-dimethyl-3,4-dihydro-2H-pyrazino[1,2-a]indol-1-one The title compound, ISP-MS: m/e=293.2, 295.2 (M+H$^+$) and $\alpha_D^{20}$=−35.7, was prepared in accordance with the general method of example 49b) from (R)-6-bromo-7-methyl-1-(2-tert-butoxycarbonylamino-1-methyl-ethyl)-1H-indole-2-carboxylic acid ethyl ester.

c) (R)-6-Bromo-7-methyl-1-(2-tert-butoxycarbonylamino-1-methyl-ethyl)-1H-indole-2-carboxylic acid ethyl ester The title compound, ISP-MS: m/e=439.5, 441.5 (M+H$^+$), was prepared in accordance with the general method of example 49c) from 6-bromo-7-methyl-1H-indole-2-carboxylic acid ethyl ester and (S)-5-methyl-2,2-dioxo-(1,2,3]oxathiazolidine-3-carboxylic acid tert-butyl ester.

d) 6-Bromo-7-methyl-1H-indole-2-carboxylic acid ethyl ester

The title compound, ISP-MS: m/e=284.2 (M+H$^+$), was prepared in accordance with the general method of example 32c) from 2-[(3-bromo-2-methyl-phenyl)-hydrazono]-propionic acid ethyl ester.

e) 2-[(3-Bromo-2-methyl-phenyl)-hydrazono]-propionic acid ethyl ester

The title compound, ISP-MS: m/e=301.2 (M+H$^+$), was prepared in accordance with the general method of example 32d), using dichloromethane as solvent, from (3-bromo-2-methyl-phenyl)-hydrazine and ethyl pyruvate.

f) (3-Bromo-2-methyl-phenyl)-hydrazine

The title compound, EI-MS: m/e=200.0 (M$^+$), was prepared in accordance with the general method of example 32e) from 3-bromo-2-methylaniline. Yellow solid. Yield 81%.

Example 51 a) (R)-7-Chloro-6-fluoro-4-methyl-1,2,3,4-tetrahydro-pyrazino[1,2-a]indole

The title compound, ISP-MS: m/e=239.2 (M+H$^+$), was prepared in accordance with the general method of example 49a) from (R)-7-bromo-4,6-dimethyl-3,4-dihydro-2H-pyrazino [1,2-a]indol-1-one.

Intermediates b) (R)-7-Chloro-6-fluoro-4-methyl-3,4-dihydro-2H-pyrazino[1,2-a]indol-1-one The title compound, EI-MS: m/e=252.1 (Mt), was prepared in accordance with the general method of example 49b) from (R)-1-(2-tert-butoxycarbonylamino-1-methyl-ethyl)-6-chloro-7-fluoro-1H-indole-2-carboxylic acid ethyl ester.

c) (R)-1-(2-tert-Butoxycarbonylamino-1-methyl-ethyl)-6-chloro-7-fluoro-1H-indole-2-carboxylic acid ethyl ester The title compound, ISP-MS: m/e=399.4 (M+H$^+$), was prepared in accordance with the general method of example 49c) from 6-chloro-7-fluoro-1H-indole-2-carboxylic acid ethyl ester and (S)-5-methyl-2,2-dioxo-[1,2,3]oxathiazolidine-3-carboxylic acid tert-butyl ester.

d) 6-Chloro-7-fluoro-1H-indole-2-carboxylic acid ethyl ester

The title compound, EI-MS: m/e=241.0 (M$^+$), was prepared in accordance with the general method of example 32c) from 2-[(3-chloro-2-fluoro-phenyl)-hydrazono]-propionic acid ethyl ester.

e) 2-[(3-Chloro-2-fluoro-phenyl)-hydrazono]-propionic acid ethyl ester

The title compound, EI-MS: m/e=258.1 (M$^+$), was prepared in accordance with the general method of example 32d) from (3-Chloro-2-fluoro-phenyl)-hydrazine and ethyl pyruvate.

f) (3-Chloro-2-fluoro-phenyl)-hydrazine

The title compound, EI-MS: m/e=160 (M$^+$), was prepared in accordance with the general method of example 32e) from 3-chloro-2-fluoroaniline.

Example 52 a) (R)-4,6,10-Trimethyl-1,2,3,4-tetrahydro-pyrazino[1,2-a]indole oxalate (R)-4,6,10-Trimethyl-3,4-dihydro-2H-pyrazino[1,2-a]indol-1-one (200 mg, 0.88 mmol) was reacted with lithium aluminium hydride in accordance with the general method of example 1a). The crude material obtained was dissolved in ether (10 mL) and treated with oxalic acid solution (20% in ethanol, 7 mL). The precipitate was collected by filtration and dried to afford the title compound (196 mg, 74%). White solid. Anal. calc. for $C_{16}H_{20}N_2O_4$: C, 63.14; H, 6.62; N, 9.20; found: C, 62.86; H, 6.87; N, 8.92%.

Intermediate b) (R)-4,6,10-Trimethyl-3,4-dihydro-2H-pyrazino[1,2-a]indol-1-one

The title compound (ISP-MS m/e=229.2 ([M+H]$^+$) was produced in accordance with the general method of example 1b) from 3,7-dimethyl-1H-indole-2-carboxylic acid ethyl ester and (S)-5-methyl-2,2-dioxo-[1,2,3]oxathiazolidine-3-carboxylic acid tert-butyl ester. White solid.

Example 53 a) (R)-8-Bromo-7-fluoro-4-methyl-1,2,3,4-tetrahydro-pyrazino[1,2-a]indole hydrochloride The title compound, m.p. 232° C., was prepared in accordance with the general method of example 26a) from (R)-8-bromo-7-fluoro-4-methyl-3,4-dihydro-1H-pyrazino [1,2-a]indole-2-carboxylic acid tert-butyl ester.

Intermediates b) (R)-8-Bromo-7-fluoro-4-methyl-3,4-dihydro-1H-pyrazino[1,2-a]indole-2-carboxylic acid tert-butyl ester The title compound, ISP-MS: m/e=383.2 ([M+H]$^+$) and m.p. 116–118° C., was prepared in accordance with the general method of example 26b) and c) from 5-bromo-2-[dimethyl-(1,1,2-trimethyl-propyl)-silanyloxymethyl]-6-fluoro-1H-indole and (S)-5-methyl-2,2-dioxo-[1,2,3]oxathiazolidine-3-carboxylic acid tert-butyl ester.

c) 5-Bromo-2-[dimethyl-(1,1,2-trimethyl-propyl)-silanyloxymethyl]-6-fluoro-H-indole The title compound, ISP-MS: m/e=302.0, 300.0 ([M+H]$^+$), was prepared in accordance with the general method of example 26 d) and e) from (4-bromo-5-fluoro-2-iodo-phenyl)-carbamic acid methyl ester.

d) (4-Bromo-5-fluoro-2-iodo-phenyl)-carbamic acid methyl ester

The tide compound, m.p. 101–102° C., was prepared in accordance with the general method of example 26f) from (4-bromo-3-fluoro-phenyl)-carbamic acid methyl ester.

e) (4-Bromo-3-fluoro-phenyl)-carbamic acid methyl ester

The title compound, m.p. 121–122° C., was prepared in accordance with the general method of example 26g) from 4-bromo-3-fluoroaniline and methyl chloroformate.

Example 54 a) (S)-(7-Trifluoromethyl-1,2,3,4-tetrahydro-pyrazino[1,2-a]indol-4-yl)-methanol To a solution of 0.240 g (S)-4-[dimethyl-(1,1,2-trimethyl-propyl)-silanyloxymethyl]-7-trifluoromethyl-3,4-dihydro-2H-pyrazino[1,2-a]indol-1-one in 3 ml THF was added 1.2 ml of a 1M solution of lithium aluminium hydride in THF. The mixture was heated to reflux for 1 h. The reaction mixture was cooled to room temperature and the 10 ml ethyl acetate and 10 ml water were added. The phases were separated and the organic phase was purified by chromatography on silica gel with 190:10:1 dichloromethane:methanol:25% aqueous ammonia eluant to yield 0.11 g of the title compound as white crystals (m.p.: 126–127° C.).

Intermediates b) (S)-4-[Dimethyl-(1,1,2-trimethyl-propyl)-silanyloxymethyl]-7-trifluoromethyl-3,4-dihydro-2H-pyrazino[1,2-a]indol-1-one To a solution of 0.700 g ethyl 6-(trifluoromethyl)indole-2-carboxylate in 7 ml DMF was added 0.13 g sodium hydride (55% in mineral oil) and the mixture was stirred at room temperature for 30 min. To the resulting solution was added 1.30 g (R)-5-[dimethyl-(1,1,2-trimethyl-propyl)-silanyloxymethyl]-2,2-dioxo-[1,2,3]oxathiazolidine-3- carboxylic acid tert-butyl ester and the mixture was stirred at room temperature for 18 h. The reaction mixture was distributed between 10% aqueous citric acid and dichloromethane and the organic phase was purified by chromatography on silica gel with dichloromethane as eluant. The product (1.15 g) was taken up in 11 ml TFA was stirred at 0° C. for 45 min. The solvent was evaporated and the residue was taken up in 10 ml methanol. To the resulting solution was added 1.00 g potassium carbonate and the mixture was stirred at room temperature for 3 h. The reaction mixture was purified by chromatography on silica gel with ethyl acetate to yield 0.36 g of the tide compound (m.p.: 143–144° C.).

Intermediate Sulfamidate
(R)-5-[Dimethyl-(1,1,2-trimethyl-propyl)-silanyloxymethyl]-2,2-dioxo-[1,2,3]oxathiazolidine-3-carboxylic acid tert-butyl ester The title compound was prepared from (R)-{3-[dimethyl-(1,1,2-trimethyl-propyl)-silanyloxy]-2-hydroxy-propyl}-carbamic acid tert-butyl ester by the general method described in example 1f). It was purified by chromatography on silica gel with gradient elution of hexane-ethyl acetate mixtures and obtained as a viscous, colorless oil. MS: m/e=396.1 (M$^+$). $\alpha_D^{20}$=+8.26.

Example 55 a) (S)-(7-Methyl-1,2,3,4-tetrahydro-pyrazino[1,2-a]indol-4-yl)-methanol

To a solution of 0.100 g 8-bromo-4-hydroxymethyl-7-methyl-3,4-dihydro-1H-pyrazino[1,2-a]indole-2-carboxylic acid tert-butyl ester in 1.00 ml toluene was added 0.014 g azabisisobutyronitrile and 0.2 ml tri-n-butyltinhydride and the mixture was heated to reflux. In intervals of ca 30 min 1.00 g tri-n-butyltinhydride was added in 0.1 ml portions and the mixture was then heated under reflux for 18 h. The mixture was cooled to room temperature, concentrated then purified by chromatography on silica gel with 2:1 hexane-:ethyl acetate as eluant. The intermediate was treated with TFA at room temperature for 30 min. The product was purified by chromatography on silica gel with 9:1:0.1 dichloromethane:methanol:ammonia as eluant to yield the tide compound as a white foam MS:217.3 (M+H)$^+$.

Intermediate b) 8-Bromo-4-hydroxymethyl-7-methyl-3,4-dihydro-1H-pyrazino[1,2-a]indole-2-carboxylic acid tert-butyl ester To a solution of 0.38 g 5-bromo-6-methyl-1H-indole-2-carbaldehyde in 5 ml dimethylformamide was added 0.090 g sodium hydride (55–65% in oil) and the mixture was stirred for 30 min at room temperature. To the resulting orange solution was added 0.884 g (R)-5-[dimethyl-(1,1,2-trimethyl-propyl)-silanyloxymethyl]-2,2-dioxo-[1,2,3] oxathiazolidine-3-carboxylic acid tert-butyl ester and the mixture was stirred at room temperature for 3 h. The reaction mixture was partitioned between 10% citric acid and ethyl acetate. The organic phase was washed with water and brine, concentrated, purified by chromatography on silica gel with hexane ethyl acetate=4:1 as eluant and dried under high vacuum to yield 0.780 g of a colorless oil. To a solution of 0.78 g of this oil in 8 ml dichloromethane were added 0.427 g sodium triacetoxyborohydride and 0.1 ml acetic acid; the resultant mixture was stirred at room temperature for 18 h. The product was purified by chromatography on silica gel with 4:1 hexane:ethyl acetate as eluant and crystallised from methanol to yield 0.320 g as white crystals. A suspension of 0.30 g of these crystals and 0.150 g ammonium fluoride in 3 ml methanol was heated to reflux for 18 h. The product was purified by chromatography on silica gel with 2:1 hexane:ethyl acetate as eluant to yield 0.186 g 8-bromo-4-hydroxymethyl-7-methyl-3,4-dihydro-1H-pyrazino[1,2-a]indole-2-carboxylic acid tert-butyl ester as a white foam MS:395.3 (M+H).

Example 56

Pharmaceutical Composition

Tablets containing the following ingredients can be manufactured in a conventional manner:

| Ingredients | Per tablet |
| --- | --- |
| Compound of formula I, e.g. compound of formula (I), e.g. (R)-6-Ethyl-4-methyl-1,2,3,4-tetrahydro-pyrazino[1,2-a]indole | 10.0–100.0 mg |
| Lactose | 125.0 mg |
| Maize starch | 75.0 mg |
| Talc | 4.0 mg |
| Magnesium stearate | 1.0 mg |

What is claimed is:

1. A chiral compound of formula (I)

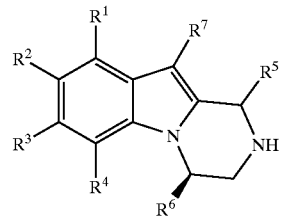

wherein

—$R^1$, $R^2$, $R^3$ and $R^4$ are independently selected from hydrogen, halogen, hydroxy, alkyl, cycloalkyl, arylalkyl, aryl, alkoxy, alkoxyalkyl, haloalkyl, haloalkoxy, aryloxy, alkylcarbonyl, arylcarbonyl, alkylthio, arylthio, alkylsulfoxyl, arylsulfoxyl, alkylsulfonyl, arylsulfonyl, amino, nitro, cyano, alkoxycarbonyl, aryloxycarbonyl, mono- and di-alkylaminocarbonyl, alkylcarbonylamino, and carboxy;

with the proviso that at least one of the moieties $R^1$, $R^2$, $R^3$ and $R^4$ is not hydrogen;

$R^5$ is hydrogen, alkyl or cycloalkyl;

$R^6$ is alkyl or cycloalkyl; and $R^7$ is hydrogen, halogen, alkyl, cycloalkyl, hydroxyalkyl, carboxyalkyl, carbamoylalkyl, alkoxycarbonylalkyl, aryloxycarbonylalkyl, formyl, alkylcarbonyl, alkoxy or alkylthio;

or a pharmaceutically acceptable salt, a hydrate, or a pharmaceutically acceptable ester thereof.

2. A process for the preparation of a chiral compound according to formula (I)

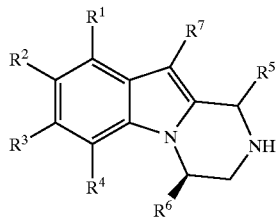

(I)

wherein $R^1$, $R^2$, $R^3$ and $R^4$ are independently selected from hydrogen, halogen, hydroxy, alkyl, cycloalkyl, arylalkyl, aryl, alkoxy, alkoxyalkyl, haloalkyl, haloalkoxy, aryloxy, alkylcarbonyl, arylcarbonyl, alkylthio, arylthio, alkylsulfoxyl, arylsulfoxyl, alkylsulfonyl, arylsulfonyl, amino, nitro, cyano, alkoxycarbonyl, aryloxycarbonyl, mono- and di-alkylaminocarbonyl, alkylcarbonylamino, and carboxy with the proviso that at least one of $R^1$, $R^2$, $R^3$ and $R^4$ is not hydrogen;

$R^5$ is hydrogen, alkyl or cycloalkyl;

$R^6$ is alkyl or cycloalkyl; and $R^7$ is hydrogen, halogen, alkyl, cycloalkyl, hydroxyalkyl, carboxyalkyl, carbamoylalkyl, alkoxycarbonylalkyl, aryloxycarbonylalkyl, formyl, alkylcarbonyl, alkoxy or alkylthio;

comprising alkylation of a compound selected from the group consisting of a)

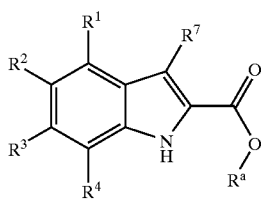

wherein $R^1$, $R^2$, $R^3$, $R^4$, and $R^7$ are as defined above, b)

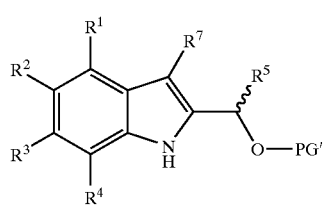

wherein $R^1$, $R^2$, $R^3$, $R^4$, $R^5$, and $R^7$ are as defined above, and PG' is hydrogen or an OH-protecting group, and c)

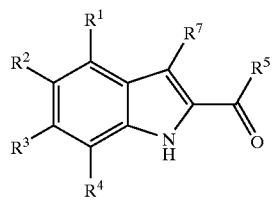

wherein $R^1$, $R^2$, $R^3$, $R^4$, $R^5$, and $R^7$ are as defined above;

with a compound of formula (III)

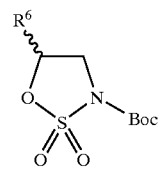

(III)

wherein $R^6$ is as defined as above.

3. The compound according to claim 1, wherein $R^6$ is alkyl.

4. The compound according to claim 3, wherein $R^6$ is methyl.

5. The compound according to claim 3, wherein $R^5$ is hydrogen.

6. The compound according to claim 3, wherein $R^7$ is hydrogen, alkyl or alkoxy.

7. The compound according to claim 6, wherein $R^7$ is hydrogen or methyl.

8. The compound according to claim 1, selected from the group consisting of:

(R)-6-ethyl-4-methyl-1,2,3,4-tetrahydro-pyrazino[1,2-a]indole;

(R)-4,6-dimethyl-1,2,3,4-tetrahydro-pyrazino[1,2-a]indole; and (R)-7-chloro-4-methyl-1,2,3,4-tetrahydro-pyrazino[1,2-a]indole;

or a pharmaceutically acceptable salt, a hydrate or a pharmaceutically acceptable ester thereof.

9. The compound according to claim 8, selected from the group consisting of:

(R)-6-ethyl-4-methyl-1,2,3,4-tetrahydro-pyrazino[1,2-a]indole;

(R)-4,6-dimethyl-1,2,3,4-tetrahydro-pyrazino[1,2-a]indole; and (R)-7-chloro-4-methyl-1,2,3,4-tetrahydro-pyrazino[1,2-a]indole.

10. A pharmaceutical composition comprising a compound of formula (I) or a pharmaceutically acceptable salt, a hydrate or a pharmaceutically acceptable ester thereof, and a pharmaceutically acceptable carrier, wherein the compound is a chiral compound of formula (I)

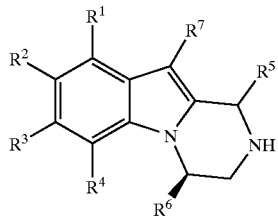

(I)

wherein
R¹, R², R³ and R⁴ are independently selected from hydrogen, halogen, hydroxy, alkyl, cycloalkyl, arylalkyl, aryl, alkoxy, alkoxyalkyl, haloalkyl haloalkoxy, aryloxy, alkylcarbonyl, arylcarbonyl, alkylthio, arylthio, alkylsulfoxyl, arylsulfoxyl, alkylsulfonyl, arylsulfonyl, amino, nitro, cyano, alkoxycarbonyl, aryloxycarbonyl, mono- and di-alkylaminocarbonyl, alkylcarbonyl amino, and carboxy, or R³ and R⁴ form together a —CH₂—CH₂—CH— group;
with the proviso that at least one of R¹, R², R³ and R⁴ is not hydrogen;
R⁵ is hydrogen, alkyl or cycloalkyl;
R⁶ is alkyl, cycloalkyl, hydroxyalkyl, or alkoxyalkyl; and
R⁷ is hydrogen, halogen, alkyl, cycloalkyl, hydroxyalkyl, carboxyalkyl, carbamoylalkyl, alkoxycarbonylalkyl, aryloxycarbonylalkyl, formyl, alkylcarbonyl, alkoxy or alkylthio.

11. The pharmaceutical composition according to claim 10, wherein
R¹, R², R³ and R⁴ are independently selected from hydrogen, halogen, hydroxy, alkyl, cycloalkyl, arylalkyl, aryl, alkoxy, alkoxyalkyl, haloalkyl, haloalkoxy, aryloxy, alkylcarbonyl, arylcarbonyl, alkylthio, arylthio, alkylsulfoxyl, arylsulfoxyl, alkylsulfonyl, arylsulfonyl, amino, nitro, cyano, alkoxycarbonyl, aryloxycarbonyl, mono- and di-alkylaminocarbonyl, alkylcarbonylamino, and carboxy;
with the proviso that at least one of the moieties R¹, R², R³ and R⁴ is not hydrogen; and
R⁶ is alkyl or hydroxyalkyl.

12. The pharmaceutical composition according to claim 11, wherein R⁶ is methyl.

13. The pharmaceutical composition according to claim 11, wherein R⁵ is hydrogen.

14. The pharmaceutical composition according to claim 11, wherein R⁷ is hydrogen, alkyl or alkoxy.

15. The pharmaceutical composition according to claim 14, wherein R⁷ is hydrogen or methyl.

16. The pharmaceutical composition according to claim 10, wherein R¹, R², R³ and R⁴ are independently selected from hydrogen, halogen, alkyl, haloalkyl, haloalkoxy and cyano or R³ and R⁴ form together a —CH₂—CH₂—CH₂— group.

17. The pharmaceutical composition according to claim 16, wherein R¹, R², R³ and R⁴ are independently selected from hydrogen, halogen, alkyl, trifluoromethyl and cyano.

18. The pharmaceutical composition according to claim 17, wherein R¹, R², R³ and R⁴ are independently selected from hydrogen, methyl, ethyl, fluoro, chloro, cyano and trifluoromethyl.

19. The pharmaceutical composition according to claim 18 wherein R⁴ is methyl or ethyl and R¹, R² and R³ are hydrogen.

20. The pharmaceutical composition according to claim 18, wherein R⁴ is fluoro, cyano or trifluoromethyl and R¹, R² and R³ are independently selected from hydrogen or methyl.

21. A pharmaceutical composition comprising a compound of formula (I) or a pharmaceutically acceptable salt, a hydrate, or a pharmaceutically acceptable ester thereof, and a pharmaceutically acceptable carrier, wherein the compound is a chiral compound of formula (I):

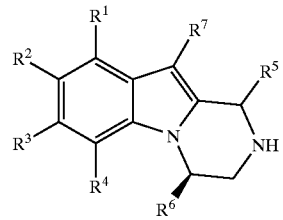

(I)

wherein
R¹, R², R³ and R⁴ are independently selected from hydrogen, methyl, ethyl, fluoro, chloro, cyano and trifluoromethyl, with the proviso that at least one of R¹, R², R³ and R⁴ is not hydrogen;
R⁵ is methyl;
R⁶ is alkyl, cycloalkyl, hydroxyalkyl or alkoxyalkyl; and
R⁷ is hydrogen or methyl.

22. The pharmaceutical composition according to claim 21, wherein the compound is (R)-6-ethyl-4-methyl-1,2,3,4-tetrahydro-pyrazino[1,2-a]indole, or a pharmaceutically acceptable salt or a hydrate thereof.

23. The pharmaceutical composition according to claim 22, wherein the compound is (R)-6-ethyl-4-methyl-1,2,3,4-tetrahydro-pyrazino[1,2-a]indole.

24. The pharmaceutical composition according to claim 21, wherein the compound is (R)-4,6-dimethyl-1,2,3,4-tetrahydro-pyrazino[1,2-a]indole, or a pharmaceutically acceptable salt or a hydrate thereof.

25. The pharmaceutical composition according to claim 24, wherein the compound is (R)-4,6-dimethyl-1,2,3,4-tetrahydro-pyrazino[1,2-a]indole.

26. The pharmaceutical composition according to claim 21, wherein the compound is (R)-7-chloro-4-methyl-1,2,3,4-tetrahydro-pyrazino[1,2-a]indole, or a pharmaceutically acceptable salt or a hydrate thereof.

27. The pharmaceutical composition according to claim 26, wherein the compound is (R)-7-chloro-4-methyl-1,2,3,4-tetrahydro-pyrazino[1,2-a]indole.

28. The pharmaceutical composition according to claim 21, wherein the compound is (R)-₄-methyl-6-trifluoromethyl-1,2,3,4-tetrahydro-pyrazino[1,2-a]indole, or a pharmaceutically acceptable salt or a hydrate thereof.

29. The pharmaceutical composition according to claim 28, wherein the compound is (R)-₄-methyl-6-trifluoromethyl-1,2,3,4-tetrahydro-pyrazino[1,2-a]indole or the hydrochloride salt thereof.

30. The pharmaceutical composition according to claim 21, wherein the compound is (R)-6-ethyl-8-fluoro-4-methyl-1,2,3,4-tetrahydro-pyrazino[1,2-a]indole, or a pharmaceutically acceptable salt or a hydrate thereof.

31. The pharmaceutical composition according to claim 30, wherein the compound is (R)-6-ethyl-8-fluoro-4-methyl-1,2,3,4-tetrahydro-pyrazino[1,2-a]indole or the hydrochloride salt thereof.

32. The pharmaceutical composition according to claim 21, wherein the compound is (R)-8-fluoro-4,7-dimethyl-1, 2,3,4-tetrahydro-pyrazino[1,2-a]indole, or a pharmaceutically acceptable salt or a hydrate thereof.

33. The pharmaceutical composition according to claim 32, wherein the compound is (R)-8-fluoro-4,7-dimethyl-1,2,3,4-tetrahydro-pyrazino[1,2-a]indole or the hydrochloride salt thereof.

34. The pharmaceutical composition according to claim 21, wherein the compound is (R)-6-fluoro-4,7-dimethyl-1,2,3,4-tetrahydro-pyrazino[1,2-a]indole, or a pharmaceutically acceptable salt or a hydrate thereof.

35. The pharmaceutical composition according to claim 34, wherein the compound is (R)-6-fluoro-4,7-dimethyl-1,2,3,4-tetrahydro-pyrazino[1,2-a]indole or the hydrochloride salt thereof.

36. The pharmaceutical composition according to claim 21, wherein the compound is (R)-$_4$-methyl-1,2,3,4-tetrahydro-pyrazino[1,2-a]indole-6-carbonitrile, or a pharmaceutically acceptable salt or a hydrate thereof.

37. The pharmaceutical composition according to claim 36, wherein the compound is (R)-$_4$-methyl-1,2,3,4-tetrahydro-pyrazino[1,2-a]indole-6-carbonitrile or the hydrochloride salt thereof.

38. The pharmaceutical composition according to claim 21, wherein the compound is (R)-4,6,10-trimethyl-1,2,3,4-tetrahydro-pyrazino[1,2-a]indole, or a pharmaceutically acceptable salt or a hydrate thereof.

39. The pharmaceutical composition according to claim 38, wherein the compound is (R)-4,6,10-trimethyl-1,2,3,4-tetrahydro-pyrazino[1,2-a]indole or the oxalate salt thereof.

40. The pharmaceutical composition according to claim 10, wherein the compound is selected from the group consisting of (R)-6-thienyl-4-methyl-1,2,3,4-tetrahydro-pyrazino[1,2-a]indole;

(R)-4,6-dimethyl-1,2,3,4-tetrahydro-pyrazino[1,2-a]indole;

(R)-7-chloro-4-methyl-1,2,3,4-tetrahydro-pyrazino[1,2-a]indole;

(R)-$_4$-methyl-6-trifluoromethyl-1,2,3,4-tetrahydro-pyrazino[1,2-a]indole;

(R)-6-ethyl-8-fluoro-4-methyl-1,2,3,4-tetrahydro-pyrazino[1,2-a]indole;

(R)-8-fluoro-4,7-dimethyl-1,2,3,4-tetrahydro-pyrazino[1,2-a]indole;

(R)-6-fluoro-4,7-dimethyl-1,2,3,4-tetrahydro-pyrazino[1,2-a]indole;

(R)-$_4$-methyl-1,2,3,4-tetrahydro-pyrazino[1,2-a]indole-6-carbonitrile; and (R)-4,6,10-trimethyl-1,2,3,4-tetrahydro-pyrazino[1,2-a]indole.

41. The pharmaceutical composition according to claim 10, wherein the compound is selected from the group consisting of (S)-(7-Methyl-1,2,3,4-tetrahydro-pyrazino[1,2-a]indol-4-yl)methanol;

(S)-(7-Trifluoromethyl-1,2,3,4-tetrahydro-pyrazino[1,2-a]indol-4-yl)-methanol; and (R)-10-Methyl-2,3,7,8,9,10-hexahydro-1H-8,10a-diaza-cyclopenta[c]fluorine;

or a pharmaceutically acceptable salt, a hydrate or a pharmaceutically acceptable ester thereof.

* * * * *

UNITED STATES PATENT AND TRADEMARK OFFICE
CERTIFICATE OF CORRECTION

PATENT NO. : 6,844,345 B2
DATED : January 18, 2005
INVENTOR(S) : Hebeisen et al.

It is certified that error appears in the above-identified patent and that said Letters Patent is hereby corrected as shown below:

Title page,
Item [73], Assignees,
"Hoffman-La Roche Inc., Nutley, NJ (US); Vernal Research Limited, Winnersh, Vernalis (GB)" should be
-- Hoffmann-La Roche Inc., Nutley, NJ (US); Vernalis Research Limited, Winnersh, Workingham (GB) --.

Column 61,
Line 22, "CH–group" should be -- CH2--group --.

Signed and Sealed this

Twenty-seventh Day of September, 2005

JON W. DUDAS
*Director of the United States Patent and Trademark Office*